US011111190B2

(12) United States Patent
Back et al.

(10) Patent No.: US 11,111,190 B2
(45) Date of Patent: Sep. 7, 2021

(54) PROCESS FOR THE DECARBOXYLATIVE KETONIZATION OF FATTY ACIDS OR FATTY ACID DERIVATIVES

(71) Applicant: RHODIA OPERATIONS, Paris (FR)

(72) Inventors: Olivier Back, Lyons (FR); Rémy Leroy, Mions (FR); Philippe Marion, Vernaison (FR)

(73) Assignee: RHODIA OPERATIONS, Aubervilliers (FR)

( * ) Notice: Subject to any disclaimer, the term of this patent is extended or adjusted under 35 U.S.C. 154(b) by 0 days.

(21) Appl. No.: 16/347,971

(22) PCT Filed: Nov. 8, 2017

(86) PCT No.: PCT/EP2017/078663
§ 371 (c)(1),
(2) Date: May 7, 2019

(87) PCT Pub. No.: WO2018/087179
PCT Pub. Date: May 17, 2018

(65) Prior Publication Data
US 2019/0292116 A1 Sep. 26, 2019

(30) Foreign Application Priority Data

Nov. 8, 2016 (EP) ..................................... 16306466
Nov. 8, 2016 (EP) ..................................... 16306469

(51) Int. Cl.
*C07B 41/06* (2006.01)
*B01J 23/745* (2006.01)
*C07C 45/48* (2006.01)
*B01J 21/10* (2006.01)

(52) U.S. Cl.
CPC .............. *C07B 41/06* (2013.01); *B01J 21/10* (2013.01); *B01J 23/745* (2013.01); *C07C 45/48* (2013.01)

(58) Field of Classification Search
CPC ......... C07B 41/06; C07C 45/48; B01J 23/745
See application file for complete search history.

(56) References Cited

U.S. PATENT DOCUMENTS 3,646,108 A 2/1972 Jones et al.
4,792,620 A * 12/1988 Paulik .................. B01J 31/0231
560/232
4,865,497 A 9/1989 Faulstich
5,416,239 A * 5/1995 Westfechtel ............ C07C 45/54
568/397
9,193,653 B1 11/2015 Hommeltoft
10,035,746 B2 7/2018 Back et al.

FOREIGN PATENT DOCUMENTS

DE 259191 C 4/1913
DE 295657 C 12/1916
EP 2468708 A1 * 6/2012 ............. C07C 45/48
EP 2468708 A1 6/2012
WO 2018033607 A1 2/2018
WO 2018087181 A1 5/2018
WO 2018087188 A1 5/2018
WO 2019161896 A1 8/2019

OTHER PUBLICATIONS

Zaragoza Dorwald, Side Reactions in Organic Synthesis, 2005, WILEY-VCH Verlag GmbH & Co. KGaA, Weinheim, Preface. p. IX . (Year: 2005).*
Norskovetal, Nature Chemistry, Towards the Computational Design of Solid Catalysts, 2009, 1, pp. 37-46. (Year: 2009).*
Gooßen, et al., "Catalytic Decarboxylative Cross-Ketonisation of Aryl- and AlkylcarboxylicAcids using Magnetite Nanoparticles", Adv. Synth. Catal. (2011) vol. 353, pp. 57-63.
Klimkiewicz, et al., "Oil Industry Waste as a Basis for Synthesis of New Type Surfactants", Polish Journal of Environmental Studies, vol. 10, No. 5 (2001), pp. 337-339.
Curtis, et al., "The Ketonization of Higher Fatty Acids with Some Observations on the Mechanism of the Reaction Part I, Studies of Waxes", Journal of the Society of Chemical Industry (1947) vol. 66, pp. 402-407.
Holleman, et al., On the Formation of Higher Aliphatic Ketones in the Thermal Decomposition of Fat—Recueil des Travaux Chimiques des Pays-Bas (1939) vol. 58, Issue 8, pp. 666-674.
Davis, et al., "Studies of Thermal Decarboxylation of Iron Carboxylates. I. Preparation of Symmetrical Aliphatic Ketones", J. Org. Chem. (1962), vol. 27, pp. 854-857.

* cited by examiner

*Primary Examiner* — Amy C Bonaparte
(74) *Attorney, Agent, or Firm* — Osha Bergman Watanabe & Burton LLP

(57) ABSTRACT

Process (P) for the decarboxylative ketonization of fatty acids, fatty acid derivatives or mixtures thereof in the liquid phase with metal compounds as catalyst wherein the fatty acids, fatty acid derivatives or mixtures thereof are added sequentially. Downstream chemistry can be realized starting from internal ketones obtained by process (P), especially in order to design and develop new surfactants.

19 Claims, No Drawings

PROCESS FOR THE DECARBOXYLATIVE KETONIZATION OF FATTY ACIDS OR FATTY ACID DERIVATIVES

CROSS-REFERENCE TO RELATED APPLICATIONS

This application is a U.S. national stage entry under 35 U.S.C. § 371 of International Application No. PCT/EP2017/078663 filed Nov. 8, 2017, which claims priority to European application No. 16306466.0, filed on Nov. 8, 2016, and European application No. 16306469.4, filed on Nov. 8, 2016. The entire contents of these applications are explicitly incorporated herein by this reference.

The present invention relates to a process for the manufacture of long chain internal ketones through decarboxylative ketonization of fatty acids or derivatives of fatty acids.

The present invention relates also to a method for the preparation of end compounds starting from the so-manufactured long chain internal ketones.

Finally, the present invention relates to the end compounds susceptible of being prepared by this method.

The conversion of acids into respective ketones by decarboxylative ketonization is a well known process which is also commercially used.

The process can be carried out in the gas phase at temperatures usually exceeding 350° C. and usually above 400° C. for fatty acids in the presence of catalytic amounts of metal oxide compounds (e.g. MgO, $ZrO_2$, $Al_2O_3$, $CeO_2$, $MnO_2$, $TiO_2$).

Carrying out the reaction in the gas phase with fatty acids with a high boiling point is difficult as the evaporation of the reactants needs very high temperatures which is detrimental for the selectivity of the process and leads to the formation of undesired by-products.

Carrying out the process in the liquid phase offers certain advantages over the reaction in the gas phase, e.g. usually higher productivities, reduced manufacturing costs and better selectivities which is important for the subsequent work-up of the reaction mixture.

German patent DE 295 657 relates to a process for the manufacture of ketones where monocarboxylic acids having a boiling point exceeding 300° C. are heated in the liquid phase with small amounts of catalytically active metal compounds, silica gels or silicates to temperatures not substantially exceeding 300° C. The organic acid is mixed with the catalytically active species and subsequently heated to the desired reaction temperature. The process is reported to yield the desired ketones in good yield and purity.

The process described in DE 295 657 does not lead to the desired ketones in good yields, however, if the fatty acid starting material comprises fatty acids or fatty acid derivatives having a boiling point of less than 300° C. (which is the case for linear fatty acids having 12 carbon atoms or less such as: lauric acid, capric acid, caprylic acid . . . ) in a more than insignificant amount.

German patent DE 259 191 relates to a process for the manufacture of ketones by heating higher fatty acids with finely distributed metals and lowering the temperature before the ketone starts to decompose. In the example stearic acid is heated with cast iron powder to a temperature of 360° C. and kept at 360° C. for about 4 h and thereafter the product is cooled down and the ketone formed is isolated. The amount of cast iron is 10 wt % based on the amount of stearic acid which corresponds to stoechiometric amounts. Again, the process as described in this reference only yields to low amounts of ketones if fatty acids having 12 carbon atoms or less are used as starting material or are present in the starting material in more than insignificant amounts.

EP2468708 relates to the decarboxylative cross-ketonization of mixtures of aryl- and alkylcarboxylic acids uring iron catalysts such as magnetite nanopowders to obtain alkylarylketones. According to the process claimed a blend of an aromatic monocarboxylic acid, a second monocarboxylic acid selected from benzylic or aliphatic monocarboxylic acids and an iron containing catalyst are heated in a non-aqueous solvent to a temperature of at least 220° C. for at least 10 h with continuous removal of water and carbon dioxide. After termination of the reaction, the blend formed is distilled under reduced pressure and the reaction product is obtained in the distillate. The use of a non-aqueous solvent is considered to be essential. The reaction times of more than 10 hours, however, are not suitable for a synthesis in an industrial scale.

In the PhD thesis of Christoph Oppel ("New methods of ketone synthesis, University of Kaiserslautern 2012), one of the inventors of the aforementioned EP 2468708, experiments for the ketonization of lauric acid with metallic mediators are described. The reaction is carried out at 340° C. with various metal compounds, including Fe and MgO and the ketone 12-tricosanone is obtained in good yields. The reaction is carried out in closed vessels saturated with nitrogen. The water and carbon dioxide formed lead to a build-up of pressure inside the closed system, and the reaction temperature of 340° C. also contributes to the build up of pressure as lauric acid at these temperatures is gaseous. Application of such a process in an industrial scale would necessitate the use of autoclaves which is expensive. The amount of metallic mediator in the examples given in the table on page 88 of the PhD thesis is 50 mol % based on the total amount of acid which corresponds to stoechiometric ratios and the entire amount of the reactants is put together initially and heated up together.

While the processes described in the prior art and referred to above yield ketones in good yields, some of them are not efficient when starting from fatty acids containing 12 atom carbons or less or mixture of fatty acids containing a significant amount of fatty acids having 12 atom carbon or less. Moreover for some of the above mentioned processes, their use in an industrial scale is hampered by problems and necessitate expensive apparatus. Thus there still exists a need for a commercially applicable process for the manufacture of ketones from fatty acids or their derivatives.

It was thus a first object of the present invention to develop a facile and easy to use process for the synthesis of ketones by decarboxylative ketonization of fatty acids or fatty acid derivatives in the liquid phase in an open reaction system, especially starting from fatty acids with 12 carbon atoms or less or mixtures of fatty acids comprising at least 10 mol %, based on the entire amount of carboxylic acids, of fatty acids with 12 carbon atoms or less or their derivatives.

Process P

This first object has been achieved with a process P for the decarboxylative ketonization of fatty acids, fatty acid derivatives or mixtures thereof in a liquid phase with metal compounds as catalysts, characterized in that a) in a first step, elementary metal or a metal compound and at least one fatty acid, at least one fatty acid derivative or a mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5 (molar ratio metal:

carboxyl group equivalent) and reacted for a period $P_1$ of from 5 min to 24 h at a temperature $T_1$ which is strictly above 270° C. and strictly below 300° C. in the substantial absence of added solvent, and b) thereafter the temperature is raised to a temperature $T_2$ which ranges from 300° C. to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the substantial absence of added solvent until the molar ratio of fatty acid, fatty acid derivative or mixture thereof to metal is in the range of from 6:1 to 99:1.

A detailed description of the process P follows.

Temperature $T_1$

Temperature $T_1$ is strictly above 270° C. but is strictly below 300° C.

Temperature $T_1$ is preferably at least 275° C., more preferably at least 280° C. and still more preferably least 285° C.

Besides, temperature $T_1$ may be at most 295° C.

Temperature $T_1$ may be from 272° C. to 298° C. or from 275° C. to 295° C.

Good results were obtained when $T_1$ ranged from 280° C. to 295° C., in particular from 285° C. to 295° C.

Temperature $T_2$

Temperature $T_2$ is in the range of from 300° C. to 400° C.

Temperature $T_2$ is preferably at least 305° C., more preferably at least 310° C.

Temperature $T_2$ is preferably at most 380° C., more preferably at most 360° C., and often at most 340° C. It may be at most 320° C.

Temperature $T_2$ in a first preferred embodiment E1 (which is exemplified in Example 1) may be of from 320° C. to 360° C., even more preferably from 320° C. to 340° C.

In embodiment E1 period $P_2$ is preferably of from 2 to 12 h, still more preferably of from 2 to 8 h.

The molar ratio of metal:carboxylate group equivalent in embodiment E1 in the first step is preferably in the range of from 1:1.0 to 1:3.0, even more preferably in the range of from 1:1.3 to 1:2.6.

In accordance with another embodiment E2 which is exemplified in Example 2, temperature $T_2$ is in the range of from 300 to 320° C., preferably in the range of from 305 to 310° C.

In embodiment E2 period $P_2$ is preferably of from 15 min to 18 h, still more preferably of from 30 min to 17 h and even more preferably of from 1 to 16 h.

Difference of temperature $T_2$ minus $T_1$ ($T_2-T_1$)

Difference of temperature $T_2$ minus $T_1$ is advantageously at least 3° C. It is preferably at least 5° C., more preferably at least 15° C.

Besides, $T_2-T_1$ is advantageously at most 100° C. It may be at most 80° C., at most 60° C. or at most 50° C.

Good results were obtained when $T_2-T_1$ ranged from 10° C. to 100° C., in particular from 15° C. to 80° C.

Period of Time $P_1$

Period of time $P_1$ may vary to a large extent depending notably on the nature of the elementary metal or metal compound and the temperature $T_1$. In any case, period of time $P_1$ is from 5 min to 24 h.

Period of time $P_1$ is preferably of at least 10 min and more preferably of at least 20 min.

Besides, period of time $P_1$ is preferably at most 12 h, more preferably at most 8 h and still more preferably at most 6 h.

Good results were obtained with period of time $P_1$ of from 10 min to 8 h, in particular of from 20 min to 6 h.

Each specified lower limit, upper limit or range for period of time $P_1$ must be considered as explicitly described in combination with each specified lower limit, upper limit or range previously specified for temperature $T_1$.

Period of Time $P_2$

Period of time $P_2$ may also vary to a large extent depending notably on the overall amount of acid or acid derivative used and temperature $T_2$. In any case, period of time $P_2$ is from 5 min to 24 h.

Period of time $P_2$ is preferably of at least 15 min, more preferably of at least 1 h and still more preferably of at least 2 h.

Besides, period of time $P_2$ is preferably of at most 18 h and more preferably of at most 16 h.

Good results were obtained with period of time $P_2$ of from 1 h to 18 h, in particular of from 2 h to 15 h.

Each specified lower limit, upper limit or range for period of time $P_2$ must be considered as explicitly described in combination with each specified lower limit, upper limit or range for temperature $T_2$.

First Step of the Process P

In the first step of the process P according to the present invention, elementary metal (or a mixture of elementary metals) or a metal compound (or a mixture of metal compounds) and the fatty acid, fatty acid derivative or mixture thereof comprising at least 10 mol %, based on the entire amount of fatty acid or fatty acid derivatives, of fatty acid having 12 carbon atoms or less or derivative of such fatty acid, are mixed in a molar ratio of from 1:0.8 to 1:3.5 (molar ratio metal:carboxylate group equivalent) and reacted for a period of time $P_1$ at a temperature $T_1$ in the substantial absence of added solvent, preferably in the absence of added solvent.

The number of carbon atoms always refers to the respective number in the free acid; if derivatives are used, the carbon number may be higher.

Suitable metals for use in the process P in accordance with the present invention are selected from the group consisting of Mg, Ca, Al, Ga, In, Ge, Sn, Pb, As, Sb, Bi, Cd and transition metals having an atomic number of from 21 to 30. Suitable metal compounds are oxides of the aforementioned metals, naphthenate salts of the aforementioned metals or acetate salts of the aformentioned metals. Magnesium and iron and their oxides, and in particular iron powder, are preferred.

The terms "fatty acids" refer to carboxylic acids containing at least 4 carbon atoms. Fatty acids are usually aliphatic. Besides, fatty acids contain generally at most 28 carbon atoms. The terms "fatty acid derivatives" refer to anhydrides made by the condensation of 2 fatty acids or to esters made by the condensation of fatty acids with alcohols.

Suitable fatty acid derivatives are esters and anhydrides of fatty acids, but the use of the free fatty acids as such is generally preferred. The esters or anhydrides in the course of the reaction are converted to the acids which then react with the metal or the metal compound. Especially in case of esters, however, alcohols are formed as a by-product which then has to be removed at a later point in time, which requires additional work and costs. However, if esters are derived from lower alcohols such as methanol, ethanol, propanol or butanol, the alcohols are removed progressively over the course of the reaction thanks to a reactive distillation.

The fatty acids or fatty acid derivatives can be used in the form of so called fatty acids or fatty acid derivatives cuts which may be obtained by the hydrolysis or alcoholysis of different natural fats and oils. Accordingly these cuts may contain various amounts of different linear fatty acids or linear fatty acid derivatives with different chain lengths. Just by way of examples fatty acid cuts obtained from coconut oil and comprising mainly $C_{12}$-$C_{18}$ fatty acids may be mentioned here. The skilled person is well aware of other fatty acid cuts obtainable form various sources and will select the best suitable starting materials based on the desired ketones.

Fatty acids having 12 carbon atoms or less, preferably of from 8 to 12 carbon atoms or derivatives of such acids (esters or anhydrides) constitute at least 10 mol % and preferably at least 15 mol % of the entire molar amount of the fatty acids mixture or fatty acids derivatives mixture used as starting material. These acids lead to ketones having a total carbon number of 23 or less which have proved to be advantageous in a number of applications. There is no specific upper limit for the amount of these fatty acids or fatty acid derivatives of acids having 12 carbon atoms or less, i.e. the starting material may also entirely consist of such fatty acids or fatty acid derivatives.

Subject to the above, preferred fatty acids for use in the process P of the present invention are hexanoic acid, isostearic acid, caprylic acid, capric acid, lauric acid, myristic acid, palmitic acid, stearic acid, arachidic acid, behenic acid, lignoceric acid, cerotic acid or mixtures thereof and preferred fatty acid derivatives are the esters and anhydrides of these acids.

It is understood that, when one and only one fatty acid or fatty acid derivative is used as the starting material, it must have 12 carbon atoms or less.

The fatty acids may comprise one or more double bonds in their chains. Examples of such fatty acids are oleic acid, linoleic acid, linolenic acid, erucic acid, palmitoleic acid and mixtures thereof.

The fatty acids may comprise one or more triple bonds in their chains. Examples of such fatty acids are tariric acid, santalbic acid and mixtures thereof.

When starting from a single fatty acid, a symmetrical ketone is obtained as the reaction product; when starting from a cut of fatty acids as described above all the ketones formed by the combination of the different alkyl groups of the starting acids are obtained and the distribution of the different mixed ketones generally follows a statistical binomial law. The reaction equation can be summarized as follows:

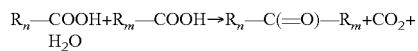

wherein $R_n$ and $R_m$ represent the aliphatic groups of the fatty acids present in the cut. It is well apparent that e.g. if three different acids are present, a total of six different ketones may be formed; three symmetrical ketones wherein $R_n$ and $R_m$ are identical and three mixed ketones with different groups $R_n$ and $R_m$. The aliphatic groups of the fatty acids are generally chosen from alkyl, alkenyl, alkanedienyl, alkanetrienyl and alkynyl groups, preferably from alkyl and alkenyl groups, more preferably from alkyl groups.

In accordance with a preferred embodiment the metal is iron powder or the metal compound is iron(II)oxide, a mixed oxide of iron(II) and iron (III) such as e.g. magnetite ($Fe_3O_4$) or an iron (III) oxide such as $Fe_2O_3$. Iron powder has some economical advantages as it is cheap and abundantly available.

During the first step of the process P in accordance with the present invention a metal carboxylate is formed as an intermediate species which in the subsequent step decomposes into the desired ketone and a metal oxide which is the active catalytic species for the subsequent conversion of the acid or acid derivative added sequentially or continuously in the second step to the desired ketone containing mixture.

If a metal is used in the first step, said metal reacts with the fatty acid to a carboxylate of the metal with simultaneous formation of hydrogen gas. If a metal oxide is used in the first step, the formation of the carboxylate is accompanied by the simultaneous formation of water. The overall equation for the carboxylate formation in the first step (for a metal having a valency of 2 as example) can be represented as follows:

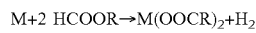

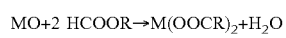

The molar ratio of metal or metal compound to the total amount of carboxylic groups in the starting material in the first step is in the range of from 1:0.8 to 1:3.5 and it is generally preferred to use a molar ratio which is sufficient to form the respective metal carboxylate and to convert all the acid or acid derivative present to the metal carboxylate, i.e. basically leaving no free carboxylic groups after formation of the carboxylate after the first step. Thus, for a bivalent metal, the molar ratio of metal to carboxylic groups is preferably about 1:2 as two equivalents of acid groups are needed to form the metal dicarboxylate of a bivalent metal. If metal oxide compounds are used instead of elementary metal, the molar ratio referred to above is calculated with the amount of elementary metal in the oxide compound. The molar amount of carboxylic groups is calculated taking into account the number of such groups in the fatty acid or fatty acid derivative which is used as a starting material. Thus, for example an anhydride of an acid comprises two carboxylate functionalities and can provide two carboxylic groups for the formation of the metal carboxylate.

The formation of the metal carboxylate in the first step can be conveniently monitored by in situ IR analysis. The carbonyl absorption band of the acid is subject to a bathochromic shift in the metal carboxylate which allows the monitoring of the reaction progress.

In accordance with a particularly preferred embodiment of the process P in accordance with the present invention, iron powder is used as metal as same is cheap and abundantly available.

Second Step of the Process P

In the second step of the process P in accordance with the present invention, the temperature is raised to temperature $T_2$ at which temperature the metal carboxylate decomposes advantageously to the desired ketone, metal oxide and carbon dioxide.

Additional fatty acid, fatty acid derivative or a mixture thereof comprising at least 10 mol %, based on the entire amount of fatty acid or fatty acid derivative, of fatty acid having 12 carbon atoms or less or derivative of such fatty acid is added in the second step, in the substantial absence of added solvent, preferably in the absence of added solvent. They may be added sequentially or continuously and they are profitably added at a rate avoiding the build-up of substantial amounts of free acid in the reaction system. Again, the progress of the reaction and the conversion of the starting materials to the carboxylates as intermediates and the ketones as final products may be conveniently monitored through appropriate methods like IR analysis.

During the second step, additional fatty acid, fatty acid derivative or a mixture thereof is added over a period of time $P_2$ which depends notably on the overall amount of acid or acid derivative used and the temperature.

For example, in embodiment E2, period of time $P_2$ is in the range of from 15 min h to 18 h, preferably of from 1 h to 16 h and particularly preferably of from 2 to 15 hours.

The total amount of fatty acid material (fatty acid or fatty acid derivative) added in the second step of the reaction is such that the overall molar ratio of metal to the amount of carboxylic groups reached at the end of the second step is in the range of from 1:6 to 1:99, i.e. the amount of metal compound is about 1 mol % to about 14 mol % and preferably of from 2 to about 13 mol % of the entire amount of fatty acid or fatty acid derivative, i.e. the metal or metal compound truly functions in a catalytic manner and is not used up in the course of the reaction. For most of the processes described in the prior art in the liquid phase the metal or metal compound has been used in amounts of more than 50 mol % and in many cases even exceeding equimolar amounts. Such high amounts of metal are not necessary in the process P in accordance with the present invention which is a technical as well as an economical advantage of the process P in accordance with the present invention over the prior art.

What has been said above for the composition of the starting fatty acid material in the first step of the process P in accordance with the present invention also applies to the second step.

The process P in accordance with the present invention is preferentially carried out in an unpressurized system, i.e. without applying superatmospheric pressure. The by-products water and carbon dioxide can be continuously removed during the course of the reaction. Suitable equipment is known to the skilled person and he will use the best suitable equipment set-up for the specific situation. Only by way of example, a so called Dean-Stark trap can be used to remove the water formed during the reaction and such removal represents a preferred embodiment of the present invention.

The process P in accordance with the present invention is carried out in the substantial absence of added solvent, preferably in the absence of added solvent. The desired ketone formed during the reaction basically acts as a solvent for the reaction. Since the ketone formed generally as a higher boiling point than the fatty acid, fatty acid derivative or mixture thereof used as starting material, this allows to carry out the reaction in the liquid phase as desired without the addition of an external solvent which would have to be removed at the end of the reaction and which is cost and labour intensive and thus undesirable.

Period of Time $P_{12}$

The additional fatty acid, fatty acid derivative or mixture thereof may be added over period of time $P_2$ under the above specified conditions immediately after the temperature has been raised to $T_2$ (which particular embodiment corresponds to $P_{12}$, as defined hereinafter, equal to 0).

Alternatively, after the temperature has been raised to $T_2$ and before the additional fatty acid, fatty acid derivative or mixture thereof is added over period of time $P_2$, said temperature may be maintained at temperature $T_2$ during a period of time $P_{12}(>0)$.

Period of time $P_{12}$ is preferably at least 30 min and more preferably at least 1 h.

Besides, period of time $P_{12}$ is preferably at most 5 h and more preferably at most 3 h.

Good results were notably obtained with $P_{12}$ ranging from 30 min to 300 min, especially from 1 h to 3 h.

Period of Time $P_{23}$

Immediately after the additional fatty acid, fatty acid derivative or mixture thereof has been added over period of time $P_2$, the temperature may be decreased, possibly down to a temperature $T_3$ which is preferably in the range of from about 5° C. to about 150° C. (which particular embodiment corresponds to $P_{23}$, as defined hereinafter, equal to 0). Temperature $T_3$ may preferably be the room temperature or a temperature slightly above the room temperature.

Alternatively, after the additional fatty acid, fatty acid derivative or mixture thereof has been added over period of time $P_2$, the temperature may be maintained at temperature $T_2$ during a period of time $P_{23}$ (>0).

Period of time $P_{23}$ is preferably at least 30 min and more preferably at least 1 h.

Besides, period of time $P_{23}$ is preferably at most 5 h and more preferably at most 3 h.

Good results were notably obtained when $P_{23}$ ranged from 30 min to 300 min, especially from 1 h to 3 h.

Recovery of the Fatty Acid Ketone and Recycling of Metallic Compounds

The internal ketone synthesized by the process P can be isolated. To this effect, conventional separation means, which are well known to the skilled person, can be used.

Thus, for example, once the fatty acid derivative or fatty acid added in the second step of the process P in accordance with the present invention has been converted, the desired ketone can be easily obtained e.g. by distillation at reduced pressure. One can take also advantage of the ferromagnetic properties of the metallic compounds formed during the reaction (such as iron oxides) to separate the metallic compounds from the ketone by applying a magnetic field. Another way to separate the products ketone from the metal compounds is through a simple filtration as the metallic compounds are not soluble in the ketones obtained as reaction product. The skilled person is aware of representative techniques so that no further details need to be given here.

The entire process P can be advantageously carried out under inert gas atmosphere and suitable inert gases are e.g. nitrogen or argon, to name only two examples.

In accordance with another preferred embodiment of the present invention, after separation of the desired ketone, the remaining residue constituted mainly of metallic compounds (for example the bottom material after distillation) can be directly reused for a second cycle of addition of fatty acid or fatty acid derivative to be converted to the desired fatty acid ketones. Overall, amounts of as low as one mole percent of metal or metal compound, relative to the amount of carboxylic acid equivalents is sufficient to obtain the desired ketones in good yield. It has been found, that up to four cycles are possible without a significant loss of catalytic activity of the metal or metal compound.

Accordingly, in another preferred embodiment of the process P of the present invention, at the end of step b) the metallic compounds are separated from the products using conventional techniques and then are recycled for the conversion of another batch of fatty acid or fatty acid derivative or a mixture thereof comprising at least 10 mol %, based on the entire amount of fatty acid or fatty acid derivative, of fatty acid having 12 carbon atoms or less or derivative of such fatty acid.

The yield of the desired ketones after step two normally exceeds 60 present, more preferably 70% and can be as high as more than 90%.

Method M of Making End Products from Internal Ketones

Internal ketones are versatile starting materials for a wide variety of end products.

It was thus another object of the present invention to build up a more facile and easier to use method for the preparation of a wide variety of end products.

This other object was achieved by a method M for the preparation of at least one end compound from at least one internal ketone, said method M comprising:

synthesizing the internal ketone by the process P as above described, and causing the internal ketone to react in accordance with a single or multiple chemical reaction scheme involving at least one reagent other than the internal ketone, wherein at least one product of the chemical reaction scheme is the end compound that is not further caused to be chemically converted into another compound.

Internal ketones obtained by the process P can be seen as easily functionalizable hydrophobic platform molecules which typically possess chain lengths that are not widely available in the nature.

Downstream chemistry of high industrial interest can be realized starting from key intermediate internal ketones, especially in order to design and develop new valuable compounds (such as ones possessing twin-tail & Gemini structures), with a particular interest for surfactants.

The chemical reaction scheme can be a single reaction scheme. A single reaction scheme can be represented as follows:

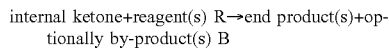
internal ketone+reagent(s) R→end product(s)+optionally by-product(s) B Alternatively, the chemical reaction scheme can be a multiple reaction scheme. A multiple reaction scheme can be represented as follows:

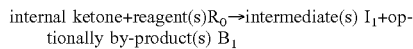
internal ketone+reagent(s)$R_0$→intermediate(s) $I_1$+optionally by-product(s) $B_1$ Optionally, N further reactions to convert intermediates into other intermediates:

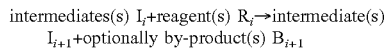
intermediates(s) $I_i$+reagent(s) $R_i$→intermediate(s) $I_{i+1}$+optionally by-product(s) $B_{i+1}$ until final intermediate(s) IF is/are obtained, wherein N is a positive integer that can be equal to 0, 1, 2, 3, 4, 5 or higher, and $I_{N+1}=I_F$

intermediate(s) $I_F$+reagent(s) $R_F$→end product(s)

All the above reactions may optionally be conducted in the presence of one or more catalyst(s). Irrespectively of whether a catalyst is present or not, reagent(s) R of above single reaction scheme and reagent(s) $R_0$ of the multiple reaction scheme are, for the purpose of the present invention, considered to react "directly" with the internal ketone.

As will be seen discussed thoroughly later on, possible reagents suitable for reacting directly with internal ketones in a single or multiple chemical reaction scheme, in particular with the internal ketones obtained by the process P, include ammonia, primary or secondary amines, mixtures of at least one aldehyde (including possibly formaldehyde) with ammonia or with at least one primary or secondary amine and alkylating agents.

Possible intermediates obtained by reacting internal ketones, in particular with the internal ketones obtained by the process P, directly with the aforementioned reagents include twin tail primary, secondary or tertiary amines, twin-tail tertiary amines themselves substituted by one or two primary, secondary or tertiary amino groups, internal ketone monoamines and internal ketone diamines such as amine Gemini compounds (typically with a central carbonyl group). All these intermediates can also be viewed as end products.

Possible end products obtained by further reacting the aforesaid intermediates with certain reagents include amphoteric compounds such as (poly)aminocarboxylates twin-tail amines, twin tail quaternary ammonium salts, internal ketone mono-quaternary ammonium salts, internal ketone di-quaternary ammonium salts such as quaternary ammonium salt Gemini compounds (typically with a central carbonyl group), aminoxide twin-tail amines, aminoxide Gemini compounds (typically with a central carbonyl group), dibetaine or disultaine twin-tail amines and betaine or sultaine Gemini compounds (typically with a central hydroxyl group). All these end products can also potentially serve as intermediates for forming still other end products.

Other particular reagents suitable for reacting directly with internal ketones ketones in a single or multiple chemical reaction scheme, in particular with the internal ketones obtained by the process P, include the diesters derived from tartaric acid, phenol and other aromatic mono- or polyalcohols, formaldehyde, pentareythritol, acrylates derivatives and hydrogen.

Possible end products obtained by reacting internal ketones, in particular the internal ketones obtained by the process P, directly with the aforementioned particular other reagents and then, if needed, with ethylene and/or propylene oxide, include anionic surfactants such as dicarboxylate salt derivatives, non-ionic surfactants (especially non-ionic surfactants having a Gemini structure) and ethylenically unsaturated monomers.

1—Making Amines from Internal Ketones 1.1) Reductive Amination to Afford Twin-Tail Amines The end product can be a twin-tail amine.

Indeed, at least one internal ketone (i.e. a single internal ketone or a mixture of internal ketones) that is advantageously synthesized by the process P can be reacted with at least one amine under reductive amination conditions to provide at least one twin-tail amine.

An internal ketone synthesized by the process P is generally a compound of formula (I)

(I)

wherein $R_n$ and $R_m$ independently represent an aliphatic group, generally a $C_3$-$C_{27}$ aliphatic group, very often a $C_3$-$C_{19}$ aliphatic group, often a aliphatic $C_6$-$C_{17}$ group.

Preferably, the aliphatic groups $R_n$ and $R_m$ are independently chosen from alkyl and alkenyl groups, generally from $C_3$-$C_{27}$ alkyl and $C_3$-$C_{27}$ alkenyl groups, very often from $C_3$-$C_{19}$ alkyl and $C_3$-$C_{19}$ alkenyl groups and often from $C_6$-$C_{17}$ alkyl and $C_6$-$C_{17}$ alkenyl groups. More preferably, $R_n$ and $R_m$ independently represent an alkyl group, generally a $C_3$-$C_{27}$ alkyl group, very often a $C_3$-$C_{19}$ alkyl group, often a $C_6$-$C_{17}$ alkyl group.

In particular, the at least one internal ketone of formula (I) can be reacted with at least one amine of formula (II) under reductive amination conditions to afford the at least one twin-tail amine of formula (III)

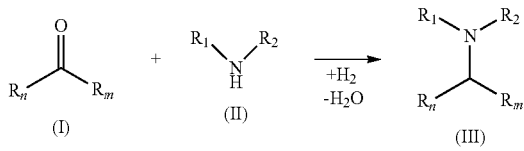

This amination reaction is preferably performed by reacting the ketone (I) and the amine (II) in the presence of a transition metal (e.g. Ni, Co, Cu, Fe, Rh, Ru, Ir, Pd, Pt) based catalyst (typically Pd/C), in a autoclave under hydrogen pressure (typically from 1 atm to 200 bar).

According to a possible embodiment, the reaction is carried out in a solvent. However, the presence of such a solvent is not compulsory and according to a specific embodiment, no solvent is used for this step. The exact nature of the solvent, if any, may be determined by the skilled person. Typical suitable solvents include, without limitation, methanol, ethanol, isopropanol, tert-butanol, THF, 2-methyltetrahydrofuran, 1,4-dioxane, dimethoxyethane, diglyme and mixtures thereof.

Besides, this step is usually carried out at a temperature ranging from 15° C. to 400° C. and may be conducted batchwise, semi-continuously or continuously and generally performed either in a batch mode or in a continuous mode using a fixed-bed catalyst (gas-solid or gas-liquid-solid process).

In the above amine formula (II), $R_1$ and $R_2$ independently represent:

hydrogen or a linear or branched hydrocarbon radical having 1 to 24 carbon atoms which can be optionally substituted and/or interrupted by one or more heteroatoms or heteroatom containing groups (for example $R_1$ and $R_2$ can be selected from H, —$CH_3$, —$CH_2CH_3$, propyl, isopropyl, butyl, sec-butyl, isobutyl and tert-butyl), ethylamine of formula —$CH_2$—$CH_2$—NR'R" wherein R' and R" independently represent hydrogen or a short alkyl group having from 1 to 6 carbon atoms (such as for example $CH_3$, $CH_2CH_3$, propyl, isopropyl),

[poly(ethylenimine)]ethylamine of formula —(—$CH_2$—$CH_2$—NH—)$_m$—$CH_2$—$CH_2$—NR'R" wherein R' and R" independently represent hydrogen or an alkyl group having from 1 to 6 carbon atoms (such as for example $CH_3$, $CH_2CH_3$, propyl, isopropyl) and m is an integer from 1 to 20, hydroxyethyl of formula —$CH_2$—$CH_2$—OH,

[poly(ethylenimine)]ethanol of formula —(—$CH_2$—$CH_2$—NH—)$_m$—$CH_2$—$CH_2$—OH wherein m is an integer from 1 to 20, a N,N-dialkylaminoalkyl radical of formula —$(CH_2)_m$—NR'R" wherein m is an integer from 3 to 20 and R' and R" independently represent hydrogen or an alkyl group having 1 to 6 carbon atoms (such as $CH_3$, $CH_2CH_3$, propyl, isopropyl), and wherein $R_1$ and $R_2$ can also form an alkanediyl radical, typically of formula —$(CH_2)_m$— wherein m ranges from 3 to 8, which can be optionally interrupted or substituted by one or more heteroatoms or heteroatom containing groups; in this case, (II) is a cyclic amine such as pyrrolidine, piperidine, morpholine or piperazine.

As examples of amines (II), one can mention: ammonia, dimethylamine, monoethanolamine, diethanolamine, ethylenediamine (EN), diethylenetriamine (DETA), triethylenetetramine (TETA), tetraethylenepentamine (TEPA), aminoethylethanolamine (AEEA) and 3,3'-Iminobis(N,N-dimethylpropylamine).

1.2) Mannich Reaction Involving Condensation with an Aldehyde and an Amine to Afford Amine Gemini Compounds The end product can be an amine Gemini compound. Typically, the amine Gemini compound comprises a central carbonyl group which, in a two-dimensional representation of the formula of this compound, can form a symmetry axis provided some conditions are met on the nature of its substituents, as will immediately be made apparent from what follows.

Indeed, the at least one internal ketone (i.e. a single internal ketone or a mixture of internal ketones) that is advantageously synthesized by the process P can be reacted with at least one aldehyde and at least one amine under Mannich reaction conditions to provide at least one ketone having one and only one of its carbonyl-adjacent carbon atoms substituted by an amine-containing group and/or at least one ketone having both of its carbonyl-adjacent carbon atoms substituted by an amine-containing group (Gemini amine).

In particular, internal ketones of formula (I)

as above defined, wherein methylene groups are adjacent to the carbonyl group on its both sides can be represented by formula (I)'

wherein $R'_n$ and $R'_m$ independently represent an aliphatic group, generally a $C_2$-$C_{26}$ aliphatic group, very often a $C_2$-$C_{18}$ group, often a $C_5$-$C_{16}$ group.

The at least one internal ketone (I') can be reacted with at least one aldehyde of formula (IV) and at least one amine of formula (II) under Mannich reaction conditions to afford at least one ketone (Va) having one and only one of its carbonyl-adjacent carbon atoms substituted by an amine-containing group and/or at least one ketone (Vb) having both of its carbonyl-adjacent carbon atoms substituted by an amine-containing group (Gemine amine).

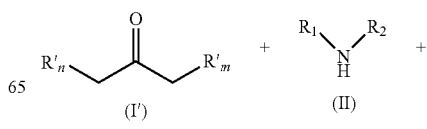

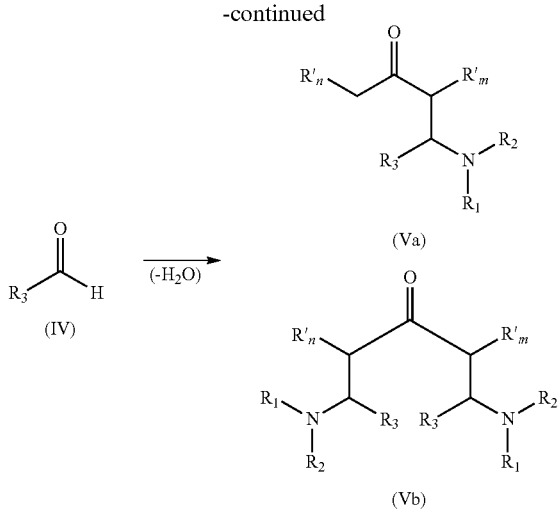

In the amine of formula (II), $R_1$ and $R_2$ are as previously defined in part 1.1.

Regarding the aldehyde (IV), $R_3$ can represent:

hydrogen or a linear or branched hydrocarbon radical having from 1 to 24 carbon atoms which can be optionally substituted and/or interrupted by one or more heteroatoms or heteroatom containing groups (for example, $R_3$ can be selected from —H, —$CH_3$, —$CH_2CH_3$, propyl, isopropyl, butyl, sec-butyl, isobutyl and tert-butyl), or an aromatic or a heterocyclic aromatic radical which can be optionally substituted by one or more branched or linear hydrocarbon radical which can optionally contain one or more heteroatom (for example, $R_3$ can be phenyl, fur-2-yl, fur-3-yl, para-hydroxyphenyl, para-methoxyphenyl or 4-hydroxy-3-methoxyphenyl).

As examples of aldehydes (IV), one can mention formaldehyde, ethanal, propanal, butanal, furfural, hydroxymethylfurfural, vanillin and para-hydroxybenzaldehyde.

The amine Gemini compound (Vb) has a central carbonyl group. In a two-dimensional representation of formula (Vb), the central carbonyl group (C═O) can form a symmetry axis when substituents $R'_m$ and $R'_n$ are identical to each other.

The Mannich reaction can be conducted under acidic conditions when the amine (II) is in its protonated form, for example as a hydrochloride salt form.

The reaction is usually carried out by contacting the ketone (I'), the aldehyde (IV) and the amine (II) (or its protonated salt which can be generated in-situ by adding a stoichiometric amount of acid), optionally in the presence of an added solvent in a reaction zone at a temperature from 15° C. to 300° C. As examples of suitable solvents to conduct the reaction, one can mention: methanol, ethanol, isopropanol, toluene, xylenes, diglyme, dioxane, THF, methyl-THF, DMSO, etc.

The amine (II) or its protonated salt as well as the aldehyde (IV) can be used in molar excess and the excess reactants can be recovered at the end of the reaction and recycled.

The reaction can also be catalyzed by the addition of a suitable Bronsted or a Lewis acid. One can mention for example: $H_2SO_4$, HCl, triflic acid, p-toluenesulfonic acid, perchloric acid, $AlCl_3$, $BF_3$, metal triflate compounds such as aluminium triflate, bismuth triflate, heterogeneous solid acids such as Amberlyst resins, zeolithes, etc.

The water generated during the reaction can be optionally trapped thanks to a Dean-Stark apparatus.

If the reaction is conducted under acidic conditions, after subsequent work-up, the products (Va) and/or (Vb) are obtained in the form of their protonated salts which can be neutralized in a second stage by the reaction with an aqueous solution of a suitable base for example: NaOH, KOH, $NH_4OH$, $Na_2CO_3$.

The desired ketones (Va) and/or (Vb) are obtained after appropriate work-up. The skilled person is aware of representative techniques so that no further details need to be given here.

2—Making Quaternary Ammoniums from Internal Ketones 2.1) Quaternization of Twin-Tail Tertiary Amines to Afford Twin-Tail Quaternary Ammonium Compounds The end product can be a twin-tail quaternary ammonium compound.

Such a twin-tail quaternary ammonium compound can be obtained as end product when at least one twin-tail amine obtained from the at least one internal ketone according to the reaction described in part 1.1 is a teriary amine. For example, when the twin-tail amine is of formula (III), this happens when $R_1$ and $R_2$ differ from a hydrogen atom.

Accordingly, at least one twin-tail tertiary amine obtained from at least one internal ketone according to the reaction described in part 1.1 can be reacted with at least one alkylating agent to obtain at least one twin-tail quaternary ammonium salt.

In particular, at least one tertiary amine (III) obtained from the at least one internal ketone (I) according to part 1.1 can be reacted with at least one alkylating agent (VI) of formula $R_4$—X to obtain at least one twin-tail quaternary ammonium salt (VII), as schemed below:

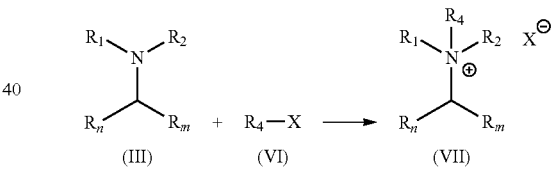

As already pointed out, amines (III) useful for use in present part 2.1 are tertiary amines. Advantageously, the tertiary amines (III) useful for use in present part 2.1 are tertiary amines wherein $R_1$ and $R_2$ independently represent a linear or branched hydrocarbon radical having from 1 to 24 carbon atoms which can be optionally substituted and/or interrupted by one or more heteroatoms or heteroatom containing groups (for example $R_1$ and $R_2$ can be selected from —$CH_3$, —$CH_2CH_3$, propyl, isopropyl, butyl, sec-butyl, isobutyl and tert-butyl) and tertiary amines wherein $R_1$ and $R_2$ form an alkanediyl radical, typically of formula —$(CH_2)_m$— wherein m ranges from 3 to 8, which can be optionally interrupted and/or substituted by one or more heteroatoms or heteroatom containing groups.

The group X contained in the alkylating agent (VI) and that constitutes the counter anion of the salt (VII) is a leaving group, typically a halide such as Cl, Br or I, methylsulfate (—$SO_4Me$), sulfate (—$SO_4^-$), a sulfonate derivative such as methanesulfonate (—$O_3S$—$CH_3$), para-toluenesulfonate (—$O_3S$—$C_7H_7$) or trifluoromethanesulfonate (—$O_3S$—$CF_3$).

In reactant (VI), $R_4$ represents a linear or branched hydrocarbon radical having 1 to 10 carbon atoms which can be optionally substituted and/or interrupted by a substituted or unsubstituted aromatic group and/or a heteroatom or heteroatom containing group. For example, $R_4$ can be: —$CH_3$, —$CH_2CH_3$, benzyl, furfuryl.

As examples of alkylating agent (VI), one can mention dimethyl sulfate, methyl chloride, methyl bromide, methyl triflate, benzyl chloride and epichlorhydrin.

This reaction can be carried out by contacting both reactants in a reaction zone at a temperature from 15° C. to 400° C., optionally in the presence of an added solvent such as methanol, ethanol, isopropanol, toluene, a xylene, diglyme, dioxane, THF, methyl-THF or DMSO. The alkylating agent can be used in stoichiometric amounts or in excess and the excess reactant can be recovered after the reaction following a suitable work-up and recycled. The skilled person is aware of representative work-up techniques so that no further details need to be given here.

2.2) Quaternization Reaction of Tertiary Amine Gemini Compounds to Afford Quaternary Ammonium Salt Gemini Compounds The end compound can be a quaternary ammonium salt Gemini compound. Typically, the quaternary ammonium salt Gemini compound comprises a central carbonyl group which, in a two-dimensional representation of the formula of this compound, can form a symmetry axis provided some conditions are met on the nature of its substituents, as will immediately be made apparent from what follows.

Such a quaternary ammonium salt Gemini compound can be obtained as end product when at least one tertiary amine Gemini compound obtained from at least one internal ketone according to the reaction described in part 1.2 is a tertiary amine Gemini compound. For example, when the amine Gemini compound is of formula (Vb), this happens when $R_1$ and $R_2$ differ from a hydrogen atom.

At least one tertiary amine Gemini compound obtained from at least one internal ketone according to the reaction described in part 1.2 can be reacted with at least one alkylating agent to obtain at least one quaternary ammonium salt Gemini compound.

For example, at least one ketone (Va) and/or at least one ketone (Vb) obtained from the at least one internal ketone (I) according to part 1.2 can be reacted with at least one alkylating agent (VI) of formula $R_4$—X to obtain respectively at least one quaternary ammonium salt (VIIIa) and/or at least one quaternary ammonium salt Gemini compound (VIIIb), as schemed below:

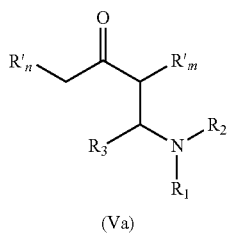
(Va)

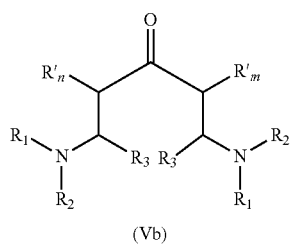
(Vb)

+ $R_4$—X
(VI)

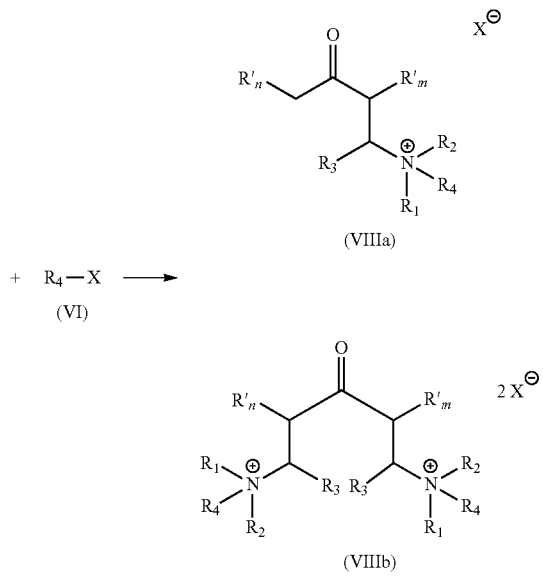
(VIIIa)

(VIIIb)

The substituents $R_1$, $R_2$, $R_4$ and the group X meet the same definitions as the ones provided in part 2.1 while the substituent $R_3$ has the same definition as in part 1.2.

This reaction can be carried out as indicated in part 2.1.

3—Making Amphoterics from Internal Ketones

The end compound can be a twin-tail (poly)aminocarboxylate.

3.1) First Synthesis of Twin-Tail (poly)aminocarboxylates

At least one twin-tail tertiary amine prepared from at least one internal ketone according to part 1.1 can be reacted with at least one alkylating agent to afford at least one amphoteric compound, notably when said twin-tail tertiary amine is itself substituted by at least one, possibly by two and only two, amino groups (—$NH_2$).

Certain amines of formula (III) that are suitable for undergoing this reaction comply with formula (III')

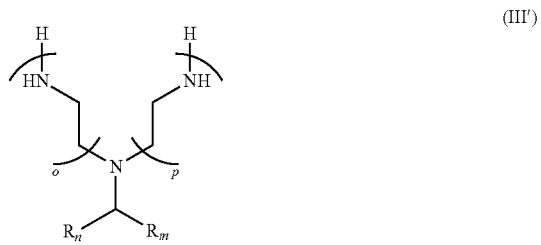
(III')

wherein $R_n$ and $R_m$ have the same meaning as in formula (I) and wherein o and p are integers from 1 to 20, preferably from 2 to 20, possibly from 4 to 20.

In particular, at least twin-tail amine of formula (III') can be reacted with at least one alkylating agent (IX) to afford at least one amphoteric compound (X), as schemed hereinafter:

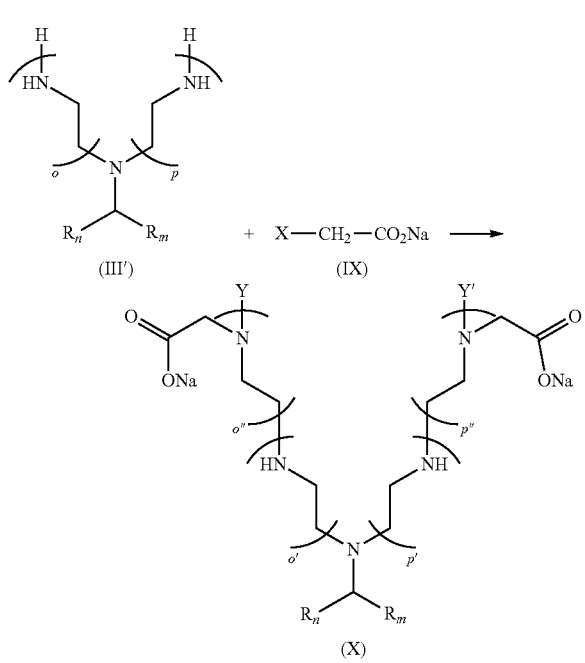

The reaction is usually conducted by contacting both reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 to 9.5. This adjustment can be done by adding required amounts of concentrated NaOH and/or HCl aqueous solutions to the reaction medium.

Importantly, by adjusting the stoichiometry of the reaction (molar excess of (IX) with respect to (III')), it is possible to adjust the average degree of alkylation of the starting amine (III') which means the average number of methylenecarboxylate groups ($-CH_2-CO_2Na$) contained in (X).

In the product (X), o', o", p' and p" are integers ranging from 0 to 20 provided that at least one of o" and p" is of at least 1. Preferably, o', o", p' and p" are integers ranging from 1 to 20, possibly from 2 to 20, and the following equalities must be respected:

$$o'+o''=o \text{ and } p'+p''=p.$$

The substituents Y and Y' can be independently a hydrogen atom or a methylenecarboxylate fragment ($-CH_2-CO_2Na$).

It has to be understood that the values of o', o", p' and p" reflect the degree of alkylation and that mixture of compounds (X) with different values for o', o", p' and p" and with different substituents Y and Y' can be obtained. Globally, one can say that when the molar amount of the alkylating agent (IX) is increased, the value of o" and p" increase (and consequently o' and p' decrease).

The group X contained in the alkylating agent (IX) is a leaving group, and has the same meaning as in part 2.1.

As an example, one can consider the reaction between the ethylenediamine-derived amine of type (III') and 2 equivalents of sodium monochloroacetate ((IX) with X=Cl). In this case, the following mixture can be obtained:

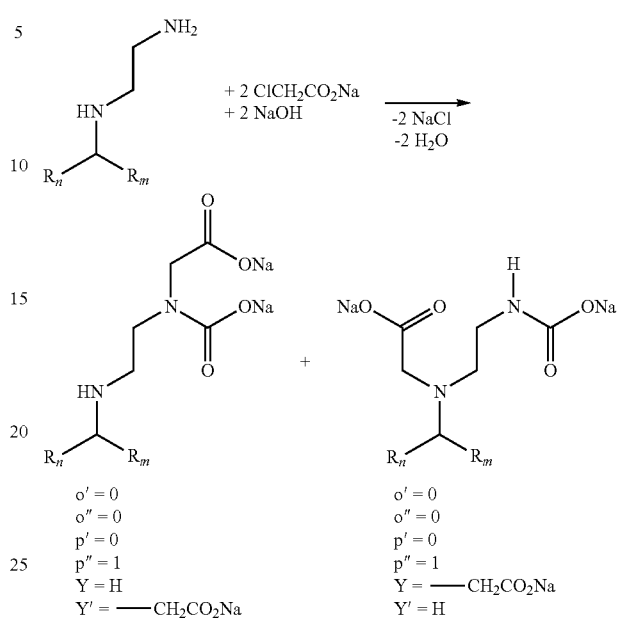

3.2) Second Synthesis of (poly)aminocarboxylates

At least one twin-tail tertiary amine prepared from at least one internal ketone according to part 1.1 can be reacted with at least one acrylate derivative (especially a hydrocarbyl acrylate of formula $CH_2=CH-CO_2A$ wherein A is hydrocarbyl, preferably $C_1$-$C_7$ hydrocarbyl, more preferably $C_1$-$C_4$ alkyl), to afford at least one amphoteric compound, notably when said twin-tail tertiary amine is itself substituted by at least one, possibly by two and only two, amino groups ($-NH_2$).

Certain amines of formula (III) that are suitable for undergoing this reaction comply with formula (III') as described in part 3.1.

In particular, the at least one twin-tail amine (III') obtained from the at least one internal ketone (I) according to part 1.1, wherein $R_n$ and $R_m$ have the same meaning as in formula (III) and wherein o and p are integers from 1 to 20, preferably from 2 to 20, possibly from 4 to 20, is reacted in a first step with at least one acrylate derivative, such as the above described hydrocarbyl acrylate, to undergo conjugate additions affording at least one ester, such as the hydrocarbyl ester of the formula (XIa')—not represented—obtained by generalizing/replacing methyl (Me) by hydrocarbyl (A substituent) in below formula (XIa). The at least one obtained ester (XIa') is then saponified in a second stage using an aqueous NaOH solution to afford at least one amphoteric compound, such as the amphoteric compound of formula (XIb')—not represented—again obtained by generalizing/replacing methyl (Me) by hydrocarbyl (A substituent) in below formula (XIb).

The following reaction scheme corresponds to the case when the acrylate derivative is $CH_2=CH-CO_2Me$ (A is methyl Me):

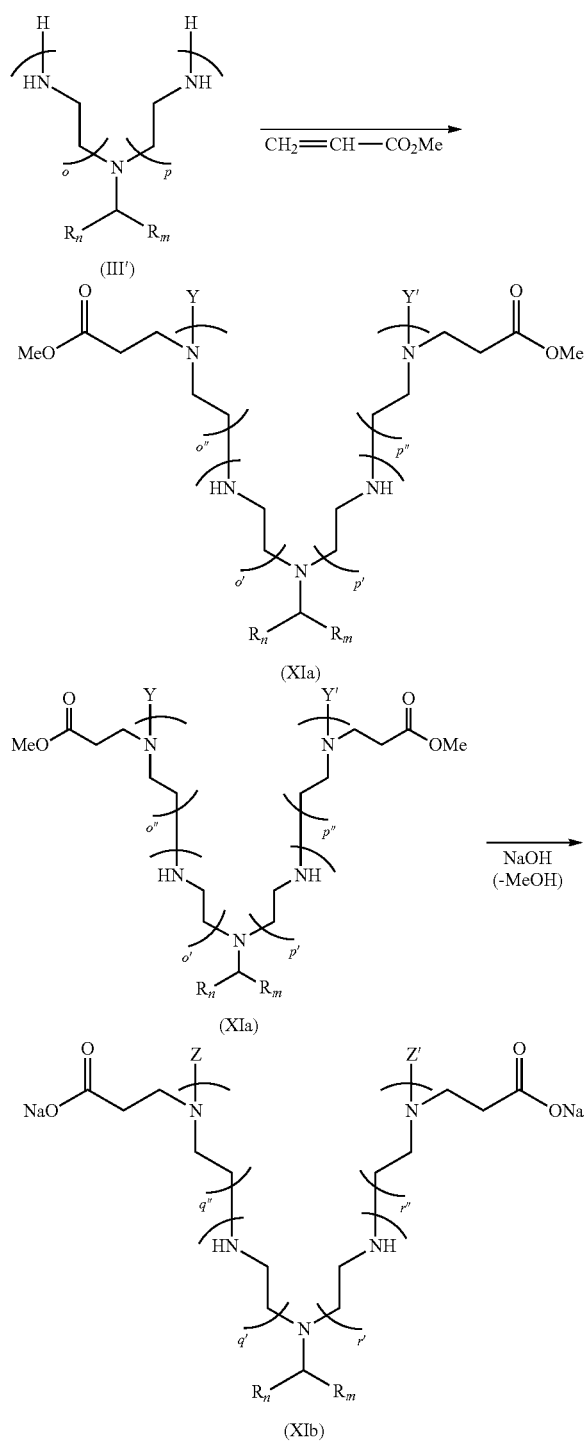

(III')

(XIa)

(XIa)

(XIb)

Typically, in the intermediate (XIa') [e.g. (XIa)], the substituents Y and Y' represent independently either a hydrogen atom or a hydrocarbyl ethylenecarboxylate fragment (—$CH_2$—$CH_2$—$CO_2$A), in particular a methyl ethylenecarboxylate fragment (—$CH_2$—$CH_2$—$CO_2$Me).

In the final amphoteric derivative (XIb') [e.g. (XIb)], the substituents Z and Z' independently represent a hydrogen atom or an ethylenecarboxylate fragment (—$CH_2$—$CH_2$—$CO_2$Na).

o', o", p' and p" in the intermediate (XIa') [e.g. (XIa)], and q', q", r' and r" in the final product (XIb') [e.g. (XIb)] are integers ranging from 0 to 20 provided that at least one of o" and p" is of at least 1 and at least one of q" and r" is of at least 1.

Preferably, o', o", p' and p" in the intermediate (XIa') [e.g. (XIa)], and q', q", r' and r" in the final product (XIb') [e.g. (XIb)] are integers ranging from 1 to 20, possibly from 2 to 20.

In addition, the following equalities must be respected:

$$o'+o''=q'+q''=o$$

$$p'+p''=r'+r''=p$$

The first step of the reaction is carried out by contacting both reactants in a reaction zone at temperature from 15° C. to 400° C. The whole amount of the reactants can be introduced directly in the reaction mixture, but in a preferred embodiment the acrylate derivative is progressively added into the reaction mixture in order to limit polymerization side reactions. The reaction can be optionally conducted in the presence of an added solvent, for example: methanol, ethanol, isopropanol, THF, dioxane, ethyl acetate, acetonitrile, etc.

The acrylate derivative can be used in excess with respect of the amine (III').

The intermediate ester (XIa') [e.g. methyl ester (XIa)] is advantageously isolated after removal of excess of acrylate derivative and optional solvents using standard techniques well known by the skilled person of the art. The second step is then carried out by contacting intermediate (XIa') with an appropriate amount of an aqueous solution of NaOH (the molar amount of NaOH is equal or higher than the molar amount of ester fragments that need to be saponified), optionally in the presence of an added solvent, such as methanol, ethanol, isopropanol, acetonitrile, DMSO or THF, and at a temperature from 15° C. to 400° C.

During the first step, the acrylate derivative can be used in a molar excess, and generally the stoichiometric ratio between amine (III') and acrylate will dictate the average degree of alkylation of the starting amine (III'), meaning the average number of hydrocarbyl ethylenecarboxylate (—$CH_2$—$CH_2$—$CO_2$A) fragments contained in the intermediate (XIa') or the like and consequently the average number of ethylenecarboxylate (—$CH_2$—$CH_2$—$CO_2$Na) fragments contained in the final amphoteric product (XIb').

It has to be understood that when the molar excess of acrylate derivative is increased during the first step, the average number of hydrocarbyl ethylenecarboxylate (—$CH_2$—$CH_2$—$CO_2$A) fragments contained in the intermediate (XIa') and the average number of ethylenecarboxylate (—$CH_2$—$CH_2$—$CO_2$Na) fragments contained in the final amphoteric product (XIb') are increased.

Usually, a mixture of intermediates (XIa') [e.g. (XIa)] with different values for o', o", p', p" and different substituents Y and Y' is obtained at the end of the first step.

Same applies for the final products (XIb') [e.g. (XIb)] where mixtures of derivatives with different values for q', q", r', r" and different substituents Z and Z' are obtained at the end of the second step.

As an example, one can consider the reaction between the ethylenediamine-derived amine of type (III') and 2.5 equivalents of methyl acrylate followed by hydrolysis.

In this case the followina mixture can be obtained:

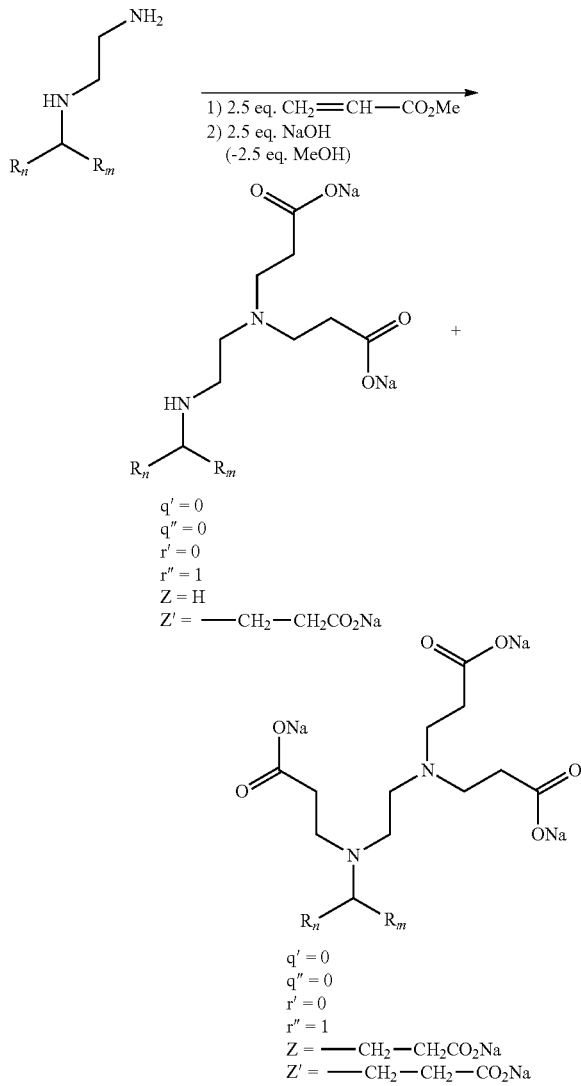

q' = 0
q" = 0
r' = 0
r" = 1
Z = H
Z' = —CH$_2$—CH$_2$CO$_2$Na q' = 0
q" = 0
r' = 0
r" = 1
Z = —CH$_2$—CH$_2$CO$_2$Na
Z' = —CH$_2$—CH$_2$—CO$_2$Na

3.3) Third Synthesis of (poly)aminocarboxylates

The reaction is conducted as described in part 3.1, except that the at least one starting amine (III) made from the at least one internal ketone (I) is an amine (III") which contains one or two terminal 2-hydroxyethyl fragment(s) (—CH$_2$—CH$_2$—OH) based on the nature of Y.

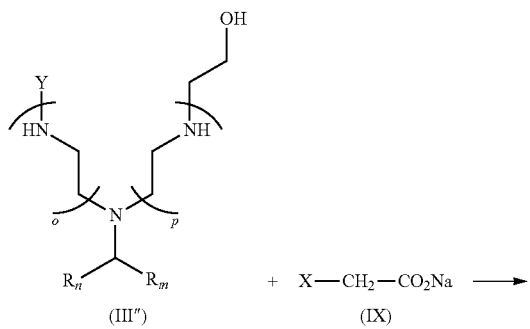

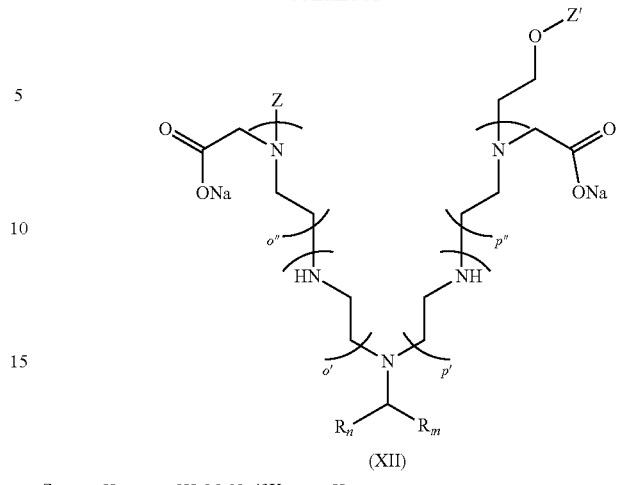

Z = —H or —CH$_2$CO$_2$Na if Y = —H
Z = —CH$_2$CH$_2$OH or —CH$_2$CH$_2$—O—CH$_2$CO$_2$Na if Y = —CH$_2$CH$_2$OH

What has been said in part 3.1 regarding the degree of alkylation applies in this case as well.

In the reaction scheme above:

o and p in the reactant (III") are integers from 1 to 20, preferably from 2 to 20, possibly from 4 to 20;

o', o", p' and p" in the product (XII) are integers ranging from 0 to 20, provided at least one of o" and p" is of at least 1; preferably, o', o", p' and p" in the product (XII) are integers ranging from 1 to 20, possibly from 2 to 20, and the following equalities must be respected:

$$o'+o''=o$$

$$p'+p''=p.$$

The substituent Y in the reactant (III''') represents a hydrogen atom or a 2-hydroxyethyl fragment (—CH$_2$—CH$_2$—OH).

The substituent Z contained in the product (XII) represents:

hydrogen or methylenecarboxylate (—CH$_2$—CO$_2$Na) when Y is hydrogen, 2-hydroxyethyl (—CH$_2$—CH$_2$—OH) or the ether fragment —CH$_2$—CH$_2$—O—CH$_2$—CO$_2$Na when Y is 2-hydroxyethyl fragment (—CH$_2$—CH$_2$—OH).

The substituent Z' represents hydrogen or methylenecarboxylate fragment —CH$_2$—CO$_2$Na.

As described in part 3.1, a mixture of products (XII) containing different numbers of methylenecarboxylate fragments (—CH$_2$—CO$_2$Na), which means different values for o', o", p' and p" and different substituents Z and Z', can be obtained.

As an example, one can consider the reaction between the aminoethylethanolamine-derived amine of type (III") and 1.5 equivalents of sodium monochloroacetate [(IX) with X=Cl]. In this case, the following mixture can be obtained:

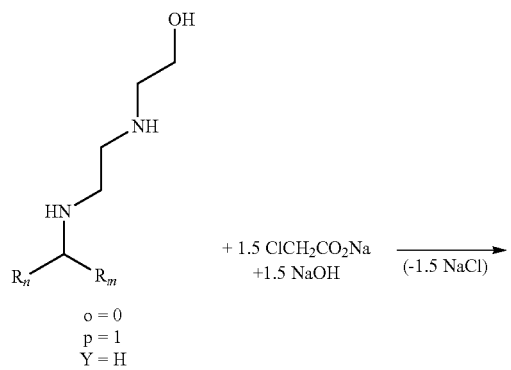

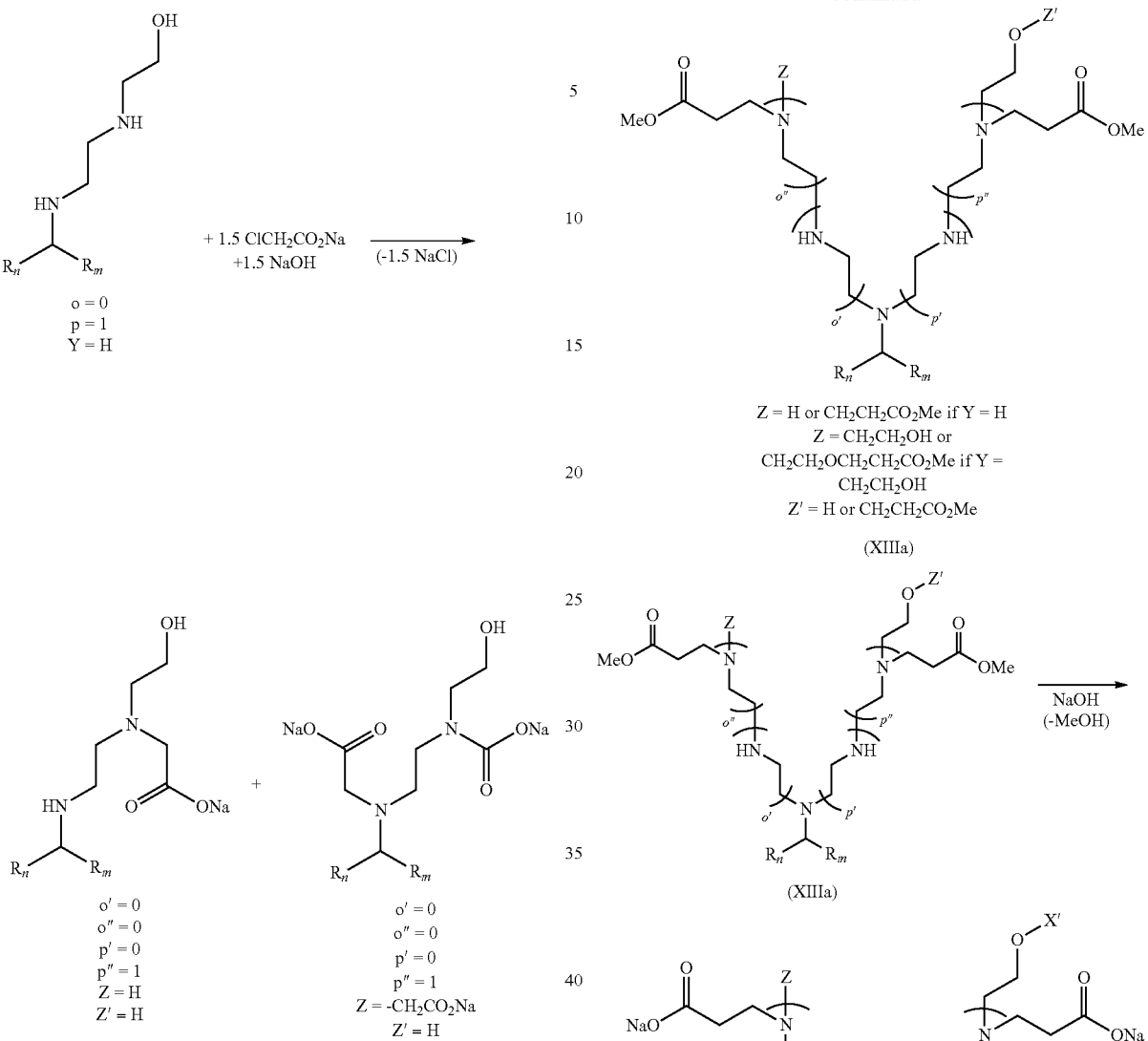

3.4) Fourth Synthesis of (poly)aminocarboxylates

The reaction is conducted as described in part 3.2, except that the at least one starting amine (III) made from the at least one internal ketone (I) is an amine (III″) which contains one or two terminal 2-hydroxyethyl fragment(s) (—CH$_2$—CH$_2$—OH) based on the nature of Y.

An exemplary reaction scheme is:

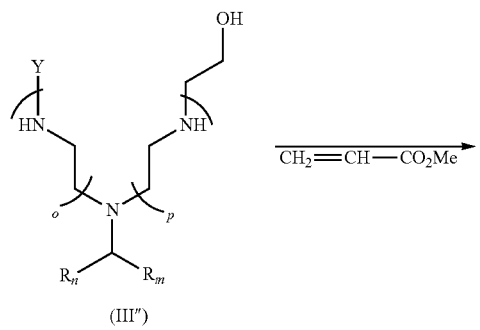

As in part 3.2, this exemplary reaction scheme can be generalized by replacing CH$_2$═CH—CO$_2$Me acrylate by hydrocarbyl acrylate of formula CH$_2$═CH—CO$_2$A, wherein A is as defined in part 3.2, and more generally by whatever acrylate derivative.

The substituent Y in the reactant (III") represents a hydrogen atom or a 2-hydroxyethyl fragment (—CH₂—CH₂—OH).

In the above reaction scheme:

o and p in the reactant (III") are integers from 1 to 20, preferably from 2 to 20, possibly from 4 to 20;

o', o", p' and p" in the intermediate (XIIIa) [or in its non represented generalization (XIIIa') wherein Me is replaced by substituent A] and q', q", r' and r" in the final product (XIIIb) [or in its non represented generalization (XIIIb') wherein Me is replaced by substituent A] are integers ranging from 0 to 20 provided that at least one of o" and p" is of at least 1 and at least one of q" and r" is of at least 1.

Preferably, o', o", p' and p" in the intermediate (XIIIa) or (XIIIa'), and q', q", r' and r" in the final product (XIIIb) or (XIIIb') are integers ranging from 1 to 20, possibly from 2 to 20.

In addition, the following equalities must be respected:

$$o'+o''=q'+q''=o$$

and $$p'+p''=r'+r''=p$$

The substituent Z in the intermediate (XIIIa') represents:

hydrogen or hydrocarbyl ethylenecarboxylate (—CH₂—CH₂—CO₂A) when Y is hydrogen, 2-hydroxyethyl fragment (—CH₂—CH₂—OH) or the ether fragment —CH₂—CH₂—O—CH₂—CH₂—CO₂A when Y is —CH₂CH₂OH.

The substituent Z' in the intermediate (XIIIa') represents either hydrogen or hydrocarbyl ethylenecarboxylate (—CH₂—CH₂—CO₂A). Thus, for example, when (XIIIa) is (XIIIa), Z' represents either hydrogen or methyl ethylenecarboxylate (—CH₂—CH₂—CO₂Me)

The substituent X in the end compound (XIIIb') [e.g. in the end compound (XIIIb)] represents:

hydrogen or ethylenecarboxylate (—CH₂—CH₂—CO₂Na) if Y is hydrogen 2-hydroxyethyl fragment (—CH₂—CH₂—OH), or the ether fragment —CH₂—CH₂—O—CH₂—CH₂—CO₂Na if Y is —CH₂CH₂OH, while the substituent X' in the end compound (XIIIb') represents either hydrogen or ethylenecarboxylate (—CH₂—CH₂—CO₂Na).

What has been said in part 3.2 regarding the impact on the alkylation degree of the molar ratio between the acrylate derivative and the substrate (III") used in the first reaction step applies here as well.

As described in part 3.2, a mixture of intermediates (XIIIa') [e.g. (XIIIa)] and a mixture of end products (XIIIb') [e.g. (XIIIb)] are usually obtained.

4—Aminoxides 4.1) Synthesis of Aminoxide Twin-Tail Amines

The end compound can be an aminoxide twin-tail amine, that is to say a twin-tail amine substituted by at least one aminoxide moiety. The aminoxide twin-tail amine can be substituted by one and only one or two and only two moiety(-ies).

At least one aminoxide twin-tail amine can be obtained from at least one twin-tail tert-amino amine (that is to say an amine that is itself substituted by at least one tert-amino group), which is itself previously obtained from at least one internal ketone.

To this effect, a certain twin-tail amine of formula (III) obtained from at least one internal ketone of formula (I) is advantageously used as reagent, namely a twin-tail tert-amino amine of formula (III'):

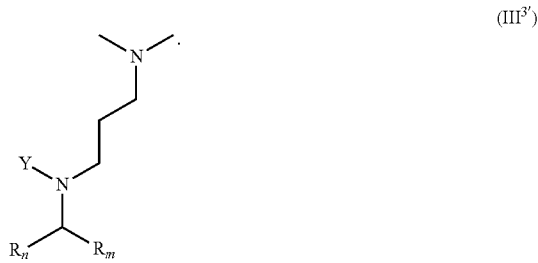

The following reaction scheme can be followed:

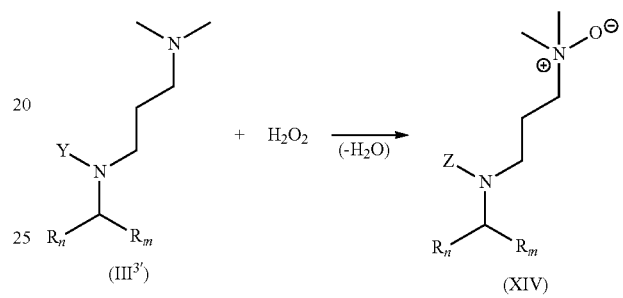

In the above scheme, Y is either hydrogen or 3-dimethylaminopropyl fragment (—CH₂—CH₂—CH₂—N(CH₃)₂); Z is hydrogen when Y is hydrogen and Z is the 3-dimethylaminoxide propyl fragment (—CH₂—CH₂—CH₂—N(CH₃)₂O) when Y is 3-dimethylaminopropyl fragment (—CH₂CH₂CH₂—N(CH₃)₂).

This reaction can be conducted by contacting the twin-tail tert-amino amine (III³') obtained from the internal ketone (I) with H₂O₂ (which can be used dissolved in aqueous solution) in a reaction zone at a temperature ranging from 15° C. to 400° C. and optionally in the presence of an added solvent. As examples of suitable solvents, one can mention methanol, ethanol, isopropanol, DMSO, acetonitrile, water, THF, dioxane or a mixture thereof.

In a preferred embodiment, H₂O₂ solution is progressively added into the reaction medium and can be used in molar excess with respect of the twin-tail tert-amino amine (III³'). The excess of H₂O₂ can be decomposed at the end of the reaction using appropriate techniques well known by the skilled person of the art.

4.2) Synthesis of Aminoxide Gemini Compounds

The end product can be an aminoxide Gemini compound. Typically, the aminoxide Gemini compound comprises a central hydroxyl group which, in a two-dimensional representation of the formula of this compound, can form a symmetry axis provided some conditions are met on the nature of its substituents, as will immediately be made apparent from what follows.

In particular, at least one aminoxide Gemini compound of formula (XVIb) can be obtained from at least one internal ketone of formula (I) using the ketone of formula (Vb) as intermediates.

It goes without saying that at least one aminoxide derivative of formula (XVIa) can likewise be obtained from at least one internal ketone of formula (I) using the ketone of formula (Va) as intermediate.

A suitable reaction scheme is described hereinafter:

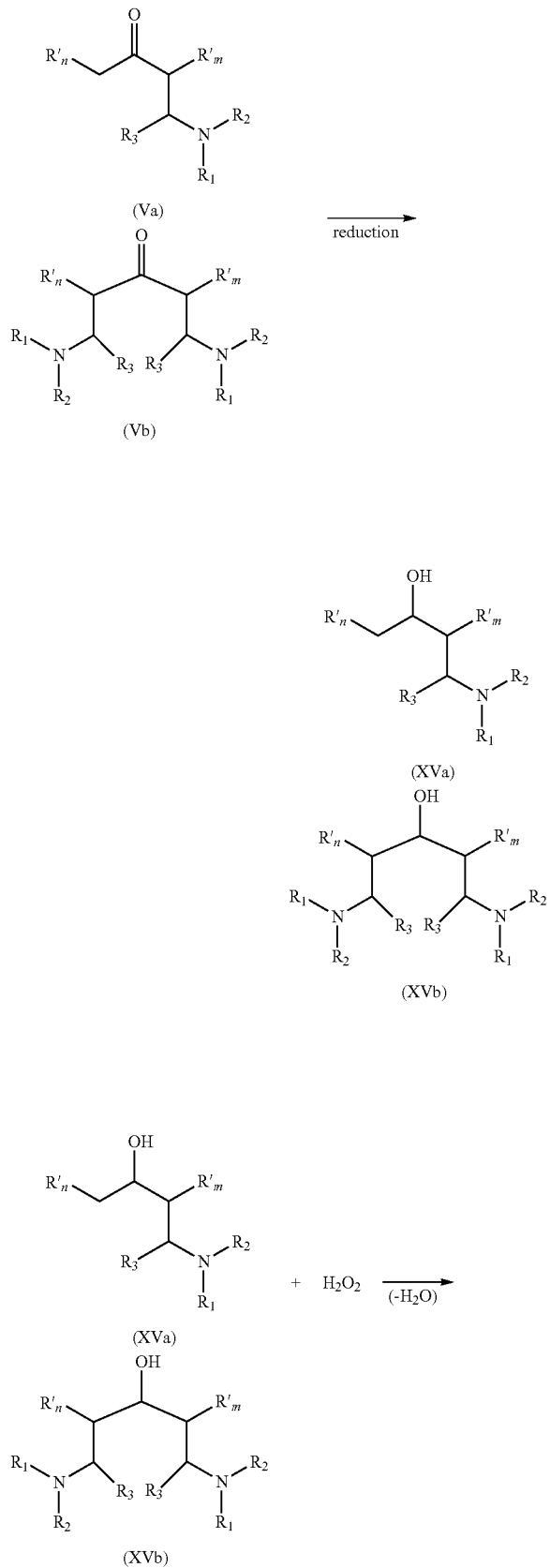

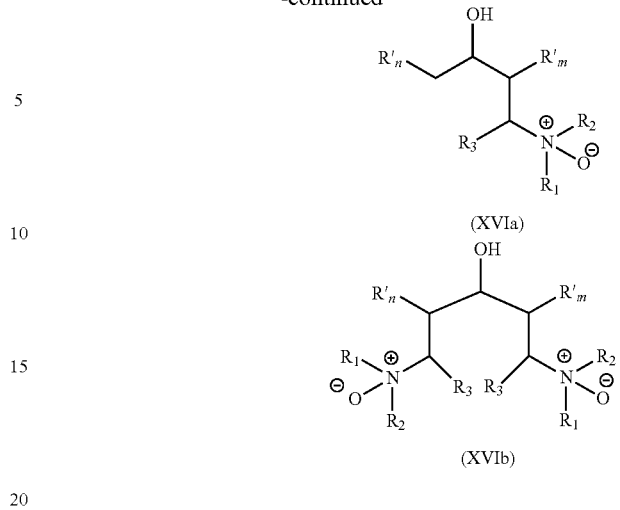

In a first step, the ketone (Va) or (Vb) or a mixture thereof is reduced respectively to the alcohol derivative (XVa) or (XVb) or a mixture thereof.

As example of suitable reductants that can be used for this first step, one can mention $H_2$. In this case, the reaction must be conducted in the presence of a suitable transition metal (e.g. Fe, Ru, Co, Rh, Ir, Ni, Pd, Pt, Cu) based catalyst (for example Pd/C). The reaction can be carried out under a hydrogen pressure (typically from 1 atm to 200 bar) and at temperature ranging from 15° C. to 400° C. Optionally, the reaction is conducted in the presence of an added solvent such as methanol, ethanol, isopropanol, tert-butanol, dioxane, dimethoxyethane, diglyme or a mixture thereof.

Another example of a suitable reductant for this first step is a secondary alcohol, preferably isopropanol which acts as a sacrificial reagent. In this case, the reaction requires the need of a metal based (e.g. Ni, Al, In, Ru, Zr) catalyst (e.g. $Al(OiPr)_3$) and acetone is formed as by-product. Importantly acetone can be removed during the reaction thanks to distillation in order to displace equilibrium toward the formation of (XVa) and (XVb).

The second step consists in the oxidation using $H_2O_2$ of the tertiary amine group of the compound of formula (XVa) and/or the compound of formula (XVb) to form respectively the aminoxide derivative of formula (XVIa) and/or the aminoxide Gemini compound of formula (XVIb).

This second step can be carried out as described in part 4.1.

$R_1$, $R_2$ and $R_3$ have the same definitions as in part 2.2.

5—Making Betaines and Sultaines from Internal Ketones 5.1) Synthesis of Dibetaine Twin-Tail Amines and Disultaine Twin-Tail Amines The end compound can be a dibetaine twin-tail amine, that is to say a twin-tail amine substituted by two betaine moieties.

The end compound can also be a disultaine twin-tail amine, that is to say a twin-tail amine comprising two sultaine moieties.

At least one dibetaine twin-tail amine can be obtained from at least one twin-tail di-tert-amino amine (that is to say a twin-tail amine that is itself substituted by two tert-amino groups)—which twin-tail di-tert-amino amine is itself previously obtained from at least one internal ketone that is advantageously synthesized by the process P—by reacting said twin-tail di-tert-amino amine with a compound of formula $$X\text{-Alk-}R_0$$

wherein:

X is a leaving group,

Alk is an alkylene group, and $R_0$ is —$CO_2M$ with M being an alkaline metal.

Methylene is preferred as the alkylene group Alk.

Na is preferred as the alkaline metal M.

The leaving group X is typically a halide such as Cl, Br or I, methylsulfate (—$SO_4Me$), sulfate (—$SO_4^-$), a sulfonate derivative such as methanesulfonate (—$O_3S$—$CH_3$), para-toluenesulfonate (—$O_3S$—$C_7H_7$) or trifluoromethane-sulfonate (—$O_3S$—$CF_3$).

At least one disultaine twin-tail amine can similarly be obtained from at least one twin-tail di-tert-amino amine which twin-tail di-tert-amino amine is itself previously obtained from at least one internal ketone, ketone that is advantageously synthesized by the process P, by reacting said twin-tail di-tert-amino amine with a compound of formula X-Alk-$R_0$ wherein:

X is a leaving group,

Alk is an alkylene group, and $R_0$ is —CH(OH)—$CH_2$—$SO_3M$ with M being an alkaline metal.

Preferred X, Alk and M to make the disultaine twin-tail amine are the same as the ones preferred to make the dibetaine twin-tail amine.

To make the dibetaine and/or the disultaine, at least one certain twin-tail amine of formula (III) is advantageously used as reactant, namely a twin-tail amine of formula (III$^{4'}$):

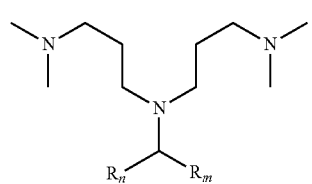

(III$^{4'}$)

wherein $R_n$ and $R_m$ have the same meaning as $R_n$ and $R_m$ of the internal ketone of formula (I).

Then, at least one dibetaine of formula (XVIIa) and/or at least one disultaine of formula (XVIIb) can be prepared from at least one twin-tail amine of formula (III$^{4'}$) according to the following scheme:

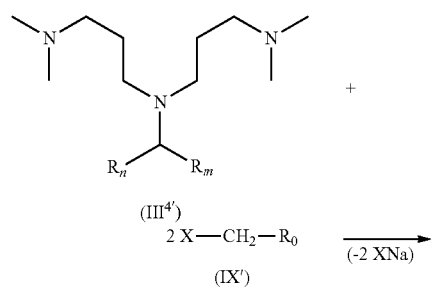

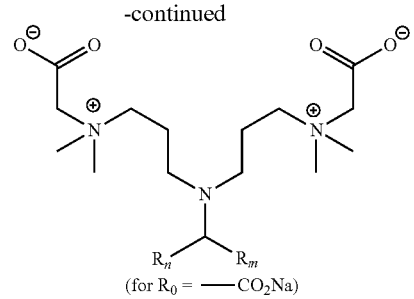

(for $R_0$ = ——$CO_2Na$)

(XVIIa)

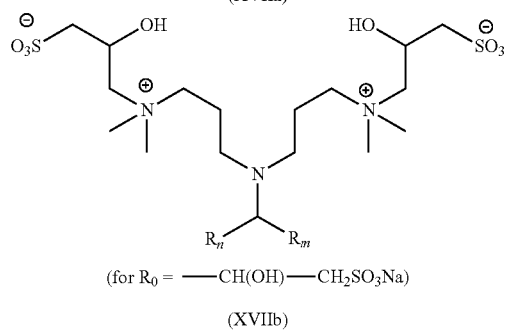

(for $R_0$ = ——CH(OH)——$CH_2SO_3Na$)

(XVIIb)

In the above reaction scheme, X is as previously defined.

The twin-tail amine (III$^{4'}$) obtained according to part 1.1 from the internal ketone (I) is reacted with the alkylating compound (IX') to afford the betaine (XVIIa) or the sultaïne (XVIIb) depending on the nature of (IX').

Betaine (XVIIa) is obtained when $R_0$ is —$CO_2Na$ and sultaine (XVIIb) is obtained when $R_0$=—CH(OH)—$CH_2$—$SO_3Na$. A mixture of betaine and sultaine is obtained when using a mixture of reagents (IX') including at least one reagent wherein $R_0$ is —$CO_2Na$ and at least one reagent wherein $R_0$=—CH(OH)—$CH_2$—$SO_3Na$.

The reaction is usually conducted by contacting the reactants in a reaction zone at temperature from 15° C. to 400° C. and optionally in the presence of an added solvent. As examples of suitable solvents, one can mention methanol, ethanol, isopropanol, DMSO, acetonitrile, water, THF, dioxane and mixtures thereof.

In a preferred embodiment, the pH of the reaction mixture is maintained during the course of the reaction from 8.5 and 9.5. This adjustment can be done by adding required amounts of concentrated NaOH and/or HCl aqueous solutions to the reaction medium during the course of the reaction.

5.2) Synthesis of Betaine Derivatives and Sultaine Derivatives, Especially of Betaine Gemini Derivatives and Sultaine Gemini Derivatives The end product can be a betaine Gemini compound or a sultaine Gemini compound. Typically, the betaine or sultaine Gemini compound comprises a central hydroxyl group which, in a two-dimensional representation of the formula of this compound, can form a symmetry axis provided some conditions are met on the nature of its substituents, as will immediately be made apparent from what follows.

At least one dibetaine and/or at least one disultaine can be obtained from at least one ketone having one or both of its carbonyl-adjacent carbon atoms substituted by an amine-containing group, in particular from at least one ketone of formula (Va) and/or at least one ketone of formula (Vb), the preparation of which from the internal ketone of formula (I) has been described in part 1.2.

At least one dibetaine and/or at least one disultaine can be obtained from at least one ketone having both of its carbonyl-adjacent carbon atoms substituted by a tert-amino-containing group, in particular from at least one ketone of formula (Vb), the preparation of which from the internal ketone of formula (I) has already been described in part 1.2.

At least one monobetaine and/or at least one monosultaine can be obtained from at least one ketone having one (and only one) of its carbonyl-adjacent carbon atoms substituted by a tert-amino-containing group, in particular from at least one ketone of formula (Va), the preparation of which from the internal ketone of formula (I) has already been described in part 1.2.

To this effect, the following reaction scheme can be followed:

The first step is identical as in part 4.2.
The second step is carried out as in part 5.1.
Betaine (XVIII) or sultaine (XIX) is obtained depending on the nature of $R_0$ in the alkylating agent (IX').
$R_1$, $R_2$ and $R_3$ have the same definition as in part 2.2.

6—Making Anionic Surfactants from Internal Ketones 6.1) Synthesis of Dicarboxylate Salt Derivatives The end compound can be an anionic surfactant.
For example, it can be a dicarboxylate salt derivative of formula

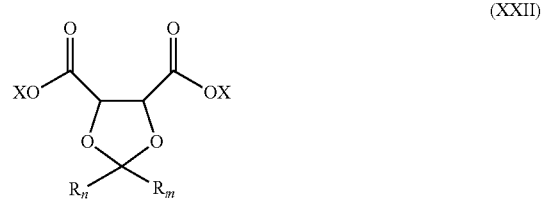

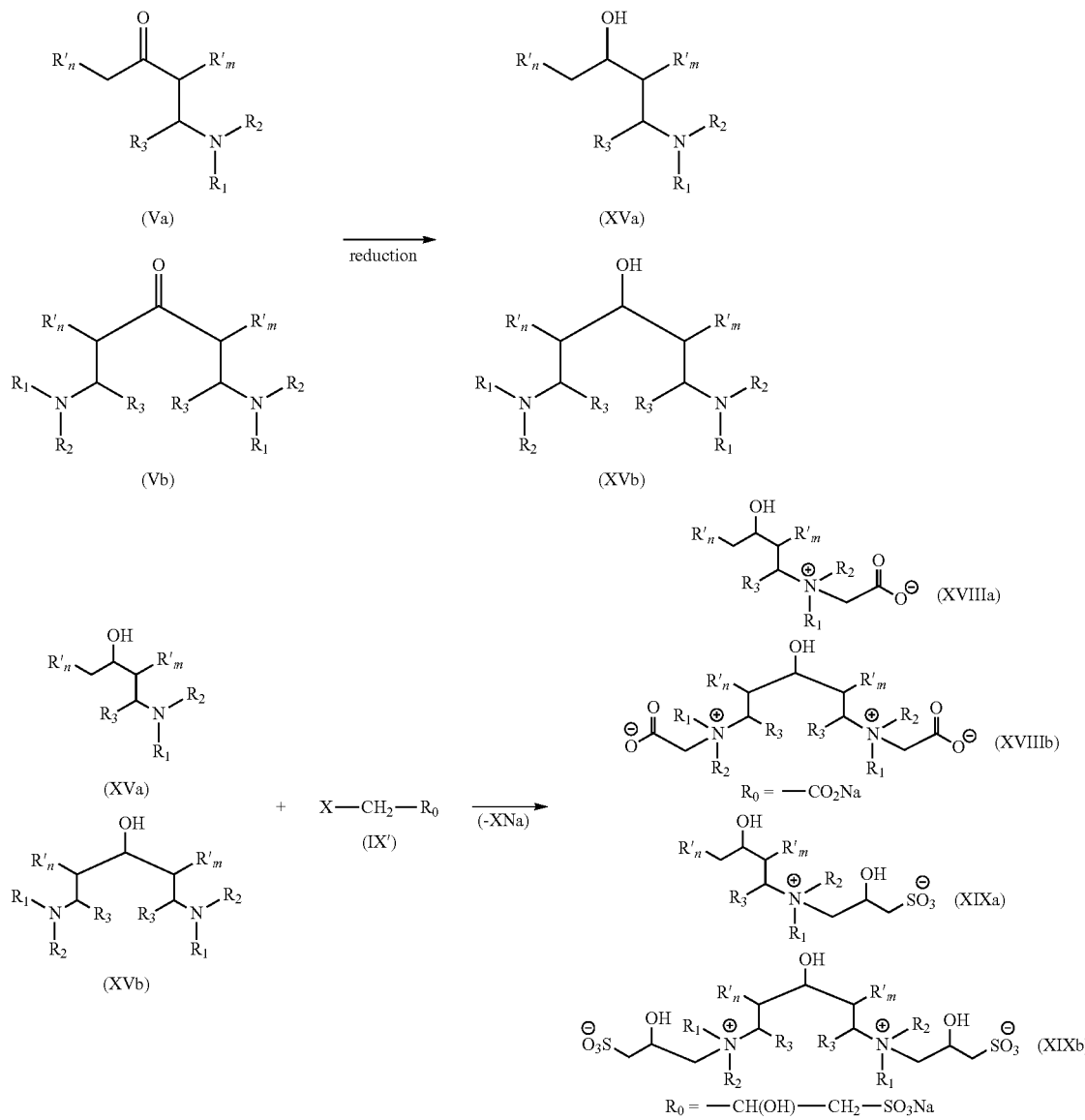

wherein X is Li, Na, K, Cs, Fr, $NH_4$, triethanolamine or other monovalent or polyvalent metal or group able to form the cationic counterion of the salt. In particular, X is Li, Na or K.

The following reaction scheme can be followed:

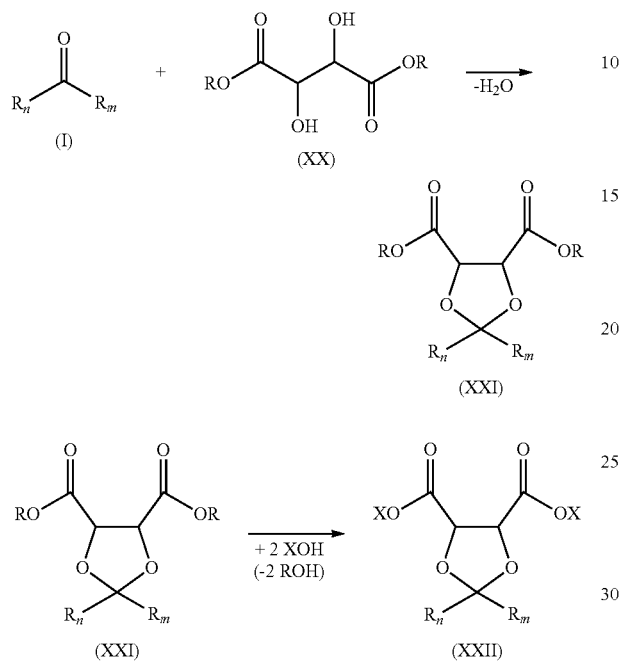

In a first step, at least one ketone (I) as previously defined is condensed with at least one diester (XX) derived from tartaric acid in which R denotes a linear or branched alkyl radical containing from 1 to 6 carbon atoms.

The reaction is realized by contacting the ketone and the diester in a reaction zone at a temperature ranging from 15° C. to 400° C. The reaction can be optionally carried out in the presence of an added solvent such as toluene, xylene, dioxane, diglyme, hexanes, petroleum ether, DMSO or a mixture thereof.

In a preferred embodiment, an acid catalyst (either Bronsted or Lewis acid) is employed to accelerate the reaction. One can mention for example $H_2SO_4$, HCl, triflic acid, p-toluenesulfonic acid, $AlCl_3$, metal triflate compounds such as aluminium triflate, bismuth triflate, heterogeneous solid acids such as Amberlyst resins and zeolithes.

The water generated during the reaction can be trapped thanks to a Dean-Stark apparatus in order to displace the reaction equilibrium toward the formation of intermediate product (XXI).

At the end of the reaction, this intermediate (XXI) can be isolated after solvent and catalyst removal using standard work-up techniques well known by the skilled person of the art so that no further detail needs to be given here.

In a second step, the ketal diester (XXI) is hydrolyzed by conducting the reaction in a basic aqueous XOH or $X(OH)_2$ solution (X as above defined, in particular X=Li, Na, K, Cs, Mg, Ca) at temperature ranging from 15° C. to 400° C. to afford the final ketal carboxylate product (XXII) along with R—OH as by-product.

7—Making Non-Ionic Surfactants from Internal Ketones

The end compound can be a non-ionic surfactant.

7.1) First Synthesis of Non-Ionic Surfactants

The end compound can be a compound of formula (XXV)

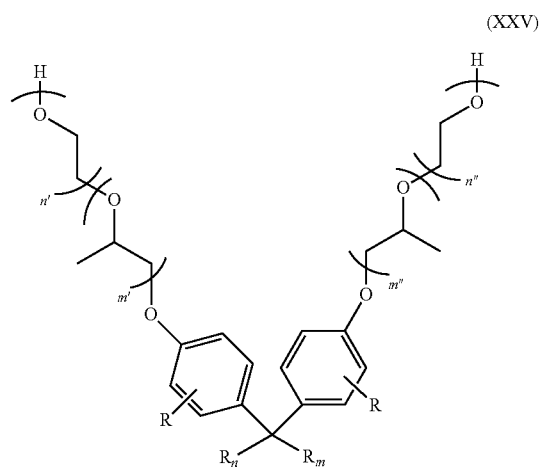

wherein:

m', m", n' and n" are integers ranging from 0 to 40 with the proviso that at least one of m', m", n' and n" is of at least 1, and m'+m"+n'+n" ranges preferably from 2 to 40, possibly from 4 to 20, $R_m$ and Rn are as defined in part 1.1, R is nil (meaning that there is no substituent on the benzene rings) or R is at least one $C_1$-$C_{24}$ alkoxy or a linear or branched $C_1$-$C_{24}$ hydrocarbon group, which alkoxy or hydrocarbon group can be optionally interrupted and/or substituted by one or more heteroatoms or heteroatom containing groups.

By specifying that R can be "at least one linear or branched hydrocarbon group", it is intended to denote that the benzene rings of compound (XXV) can be substituted not only by one substituent but also by several one linear or branched hydrocarbon substituents.

Two examples of possible R substituents are methyl and methoxy.

The following reaction scheme can be followed:

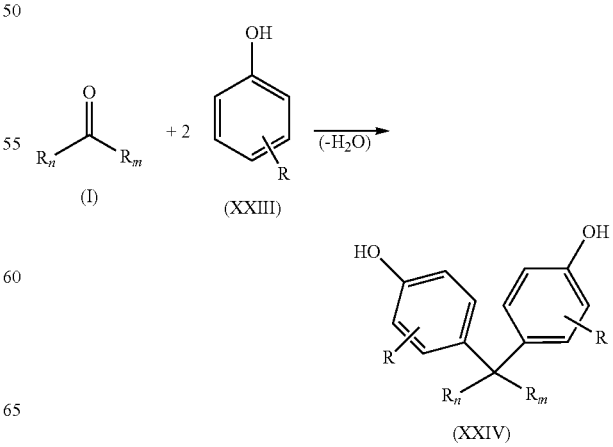

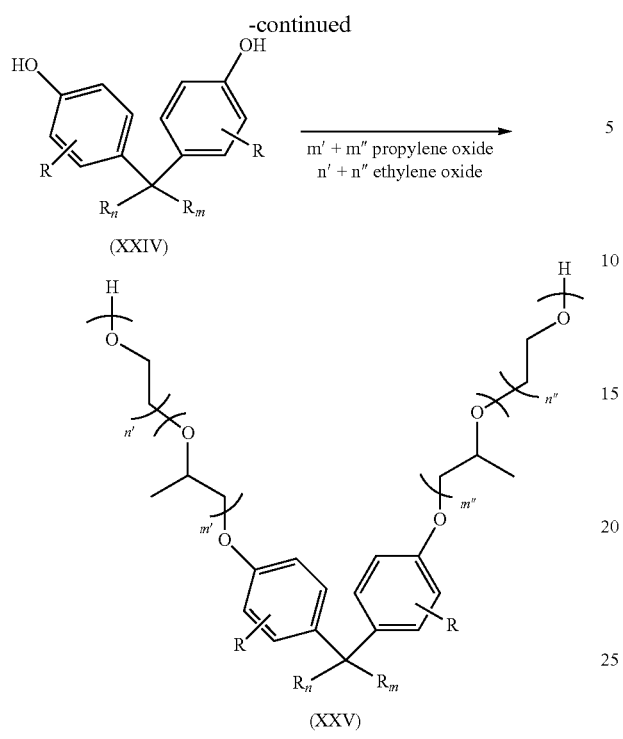

(XXIV)

(XXV)

Accordingly, in a first step, at least one ketone (I) is first condensed with 2 equivalents of a substituted or unsubstituted phenolic compound (XXIII) (e.g. when R is nil, (XXIII) is phenol, while when R is methyl or methoxy, (X)(III) is respectively cresol or guaiacol) in order to afford the bi-phenolic derivative (XXIV).

The reaction can be carried out by contacted both reactants in a reaction zone at a temperature ranging from 15° C. to 400° C. optionally in the presence of an added solvent. An excess of the phenolic derivative (XXIII) can be used for this reaction and the reactant in excess can be removed later during the subsequent work-up and recycled.

An acid catalyst (either Bronsted or Lewis acid) can be employed to accelerate the reaction. One can mention for example $H_2SO_4$, HCl, triflic acid, p-toluenesulfonic acid, $AlCl_3$, metal triflate compounds such as aluminium triflate and bismuth triflate, heterogeneous solid acids (such as Amberlyst resins, zeolithes, etc.

Water generated during this step can be trapped thanks to a Dean-Stark apparatus is order to drive the reaction equilibrium toward the desired product (XXIV).

The intermediate product (XXIV) can be isolated using standard work-up techniques well known by the skilled person of the art so that no further detail needs to be given here.

In a second step, the di-phenolic derivative (XXIV) is condensed with m'+m" equivalents of propylene oxide and/ or by, possibly followed by, n'+n" equivalents of ethylene oxide using standard conditions for alkoxylation of di-phenolic derivatives in order to afford the non-ionic surfactant (XXV).

Other non-ionic surfactants than (XXV) can be prepared according to the same reaction scheme but using another aromatic alcohol than (XXIII) as reagent.

As examples of other aromatic alcohols, one can mention naphtols and aromatic diols such as catechol and resorcinol.

7.2) Second Synthesis of Non-Ionic Surfactants

The end compound can be a non-ionic surfactant of formula (XXVIIa)

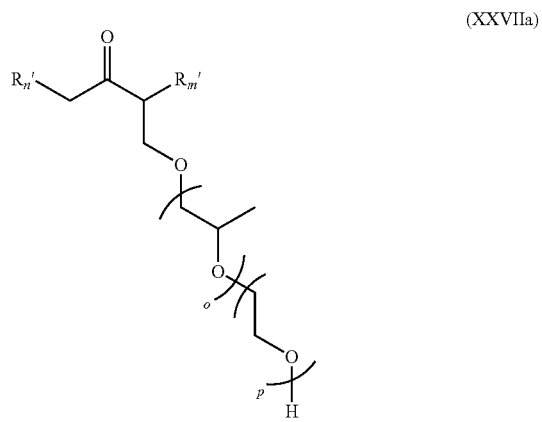

(XXVIIa)

or a non-ionic surfactant of formula (XXVIIb)

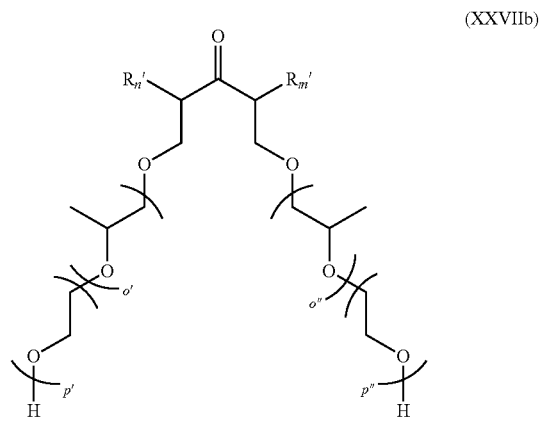

(XXVIIb)

wherein:

$R'_m$ and $R'_n$ represent an aliphatic group, generally a $C_2$-$C_{26}$ aliphatic group, very often a $C_2$-$C_{18}$ group, often a $C_5$-$C_{16}$ group, o, o', o", p, p' and p" are as defined hereinafter.

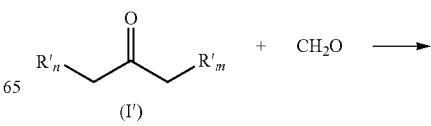

(I')

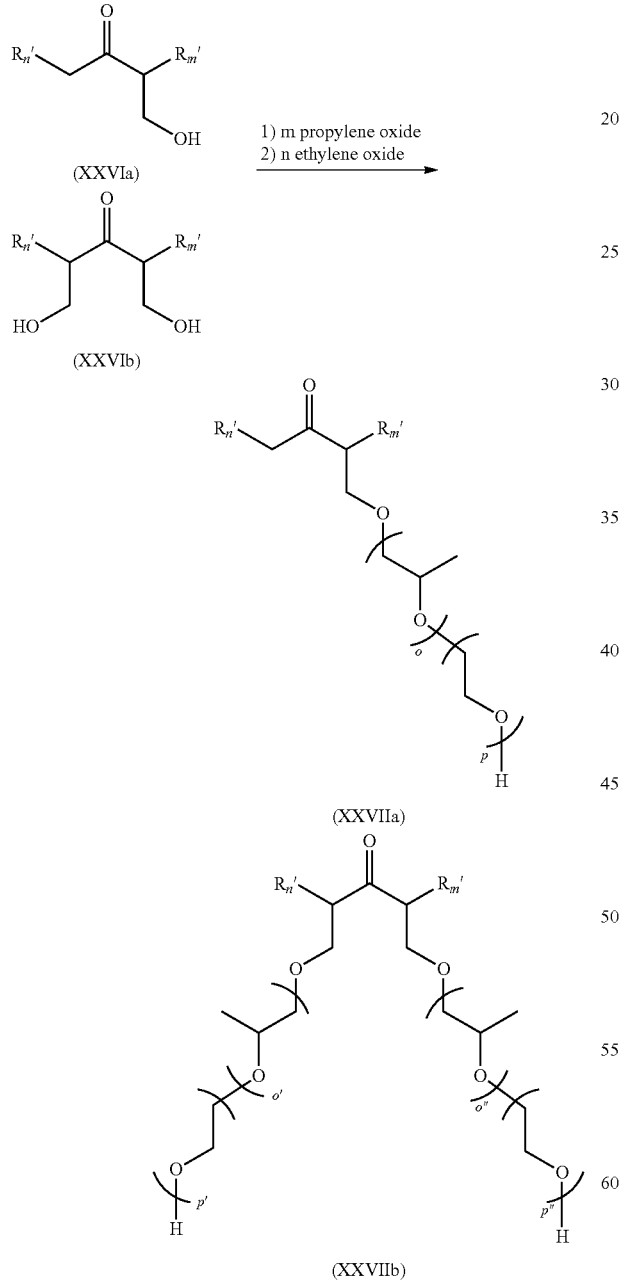

In the above scheme, "1) m propylene oxide|2) n ethylene oxide" should be broadly understood, not implying that both propoxylation and ethoxylation must take place (otherwise said, m or n can be equal to 0), a fortiori not implying that propoxylation must take place before ethoxylation, although this is an embodiment that may be preferred.

In a first step, at least one ketone (I') is condensed with formaldehyde ($CH_2O$). The condensation takes advantageously place in a reaction zone at a temperature ranging from −20° C. to 400° C. The reaction can be carried out in the presence of a basic catalyst, such as for example NaOH, KOH, MgO, $Na_2CO_3$, NaOMe, NaOEt, tBuOK or $NEt_3$. The reaction can optionally be carried out in a solvent such as methanol, ethanol, isopropanol, DMSO, THF, methyltetrahydrofuran, toluene, a xylene, water, dioxane or a mixture thereof.

For this first reaction step, formaldehyde can be used in excess and the reactant in excess can be recovered and recycled.

The aldol products (XXVIa), (XXVIb) or their mixture can be isolated using standard work-up techniques well known by the skilled person of the art.

In the second step, at least one product (XXVIa) and/or (XXVIb) is/are condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactants (XXXIIa) and/or (XXVIIb).

In the above equation scheme, m and n are integers ranging from 0 to 40 but m and n cannot be both equal to 0.

o, p, o', p', o" and p" are integers ranging from 0 to 40 and the following equalities must be respected:

$$o+o'+o''=m$$

$$p+p'+p''=n$$

7.3) Third Synthesis of Non-Ionic Surfactants

The end compound can be a compound of formula (XXIX)

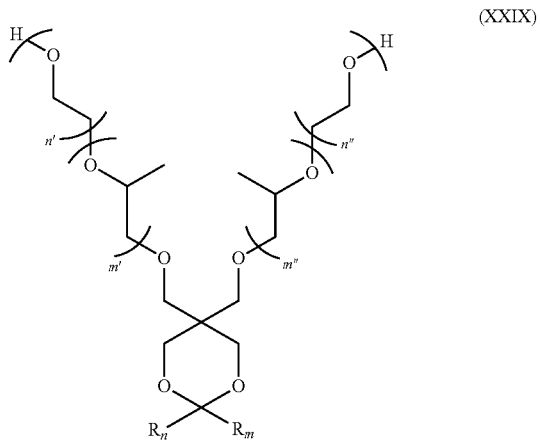

wherein:

$R_n$ and $R_m$ are as defined in part 1.1, m', m", n' and n" are as defined hereinafter.

To this end, in a first step, at least one internal ketone (I) is condensed with pentaerythritol to afford at least one intermediate (XXVIII).

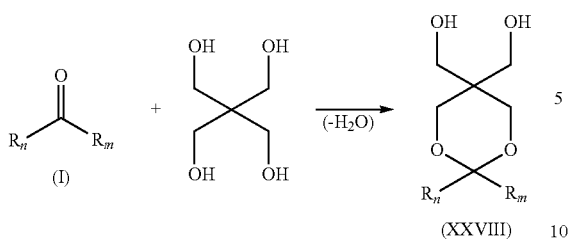

(XXVIII)

This reaction is advantageously carried out by contacted both reactants in a reaction zone at a temperature ranging from 15° C. to 400° C. The reaction can be optionally carried out in the presence of an added solvent such as toluene, xylene, dioxane, diglyme, hexane, petroleum ether, DMSO or a mixture thereof.

In a preferred embodiment, an acid catalyst (either Bronsted or Lewis acid) is employed to accelerate the reaction. One can mention for example: $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolithes, etc.

The water generated during the reaction can be trapped thanks to a Dean-Stark apparatus in order to displace the reaction equilibrium toward the formation of the at least one intermediate (XXVIII).

At the end of the reaction, this intermediate (XXVIII) can be isolated after solvent and catalyst removal using standard work-up techniques well known by the skilled person of the art so that no further detail needs to be given here.

In the second step, the at least one intermediate (XXVIII) is condensed with m+n equivalents of alkylene oxide (m equivalents of propylene oxide and/or n equivalents of ethylene oxide, e.g. m equivalents of propylene oxide followed by n equivalents of ethylene oxide) using standard conditions for alkoxylation of alcohols in order to afford the non-ionic surfactant (XXIX)

The reaction taking place in the second step can be represented as follows:

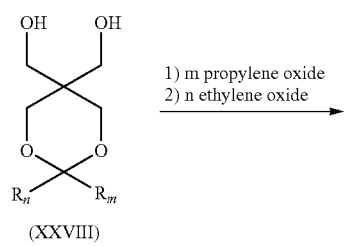

(XXVIII)

1) m propylene oxide
2) n ethylene oxide

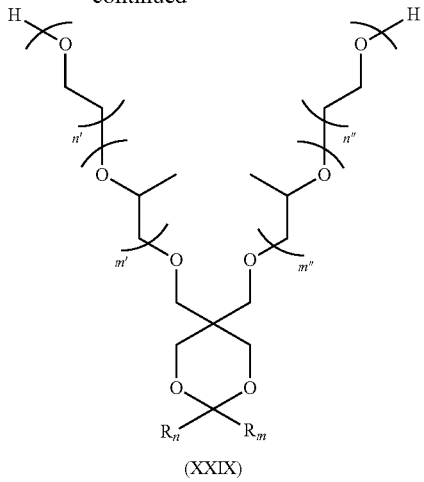

(XXIX)

In the above reaction scheme, "1) m propylene oxide|2) n ethylene oxide" should be broadly understood, not implying that both propoxylation and ethoxylation must take place (otherwise said, m or n can be equal to 0), a fortiori not implying that propoxylation must take place before ethoxylation, although this is an embodiment that may be preferred.

As a matter of fact, in the above reaction scheme, m and n are integers ranging from 0 to 40 provided at least one of m and n is of at least 1.

m', m", n' and n" are integers ranging from 0 to 40 and the following equalities must be respected:

$$m'+m''=m$$

$$n'+n''=n$$

8—Making Intermediates and Monomers from Internal Ketones 8.1) Synthesis of Beta Diketones The at least one end compound can be a beta diketone of formula (XXXIa) and/or a beta diketone of formula (XXXIb), such as the reaction products of the following reaction involving at least one internal ketone of formula (I'):

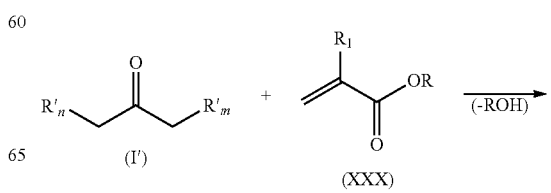

(I')  (XXX)

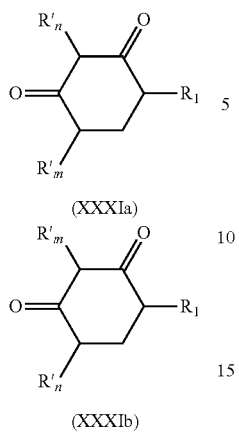

(XXXIa)

(XXXIb)

Accordingly, at least one ketone (I') with $R_m$ and Rn as previously defined is reacted with at least one acrylate derivative (XXX) to obtain at least one diketone (XXXIa) and/or at least one diketone (XXXIb).

In the above reaction scheme, the substituent R is selected from a linear or branched hydrocarbon radical having from 1 to 24 carbon atoms which can be optionally substituted and/or interrupted by one or more heteroatoms or heteroatom containing groups. For example, R can be selected from —$CH_3$, —$CH_2CH_3$, propyl, isopropyl, butyl, sec-butyl, isobutyl and tert-butyl.

The substituent $R_1$ is selected from hydrogen and a linear or branched hydrocarbon radical having from 1 to 24 carbon atoms which can be optionally substituted and/or interrupted by one or more heteroatoms or heteroatom containing groups. For example, $R_1$ can be H, methyl, ethyl, propyl, isopropyl, butyl, sec-butyl, isobutyl or tert-butyl.

The reaction zone takes advantageously place at a temperature ranging from 15° C. to 400° C.

At least one equivalent relative to the ketone (I') of a base may be required for the reaction to occur. As example of suitable bases to carry out the reaction, one can mention NaOMe, tert-BuOK, NaOEt, KOH or NaOH.

During the course of the reaction an alcohol R—OH is generated which can optionally be distilled off from the reaction mixture.

In addition, a suitable solvent can be used for the reaction such as for example methanol, ethanol, isopropanol, THF, DMSO, methyltetrahydrofuran, dioxane or diglyme.

At the end of the reaction, the at least one diketone compound (XXXIa) and/or the at least one diketone compound (XXXIb) are possibly obtained in their deprotonated form so that an acidic quench is needed to recover the neutral derivatives (XXXIa) and/or (XXXIb).

8.2) Synthesis of a First Monomer

The at least one end compound can be a compound of formula (XXXIII). Such a compound, which contains an ethylenic carbon-carbon double bond, is suitable to undergo a radical polymerization.

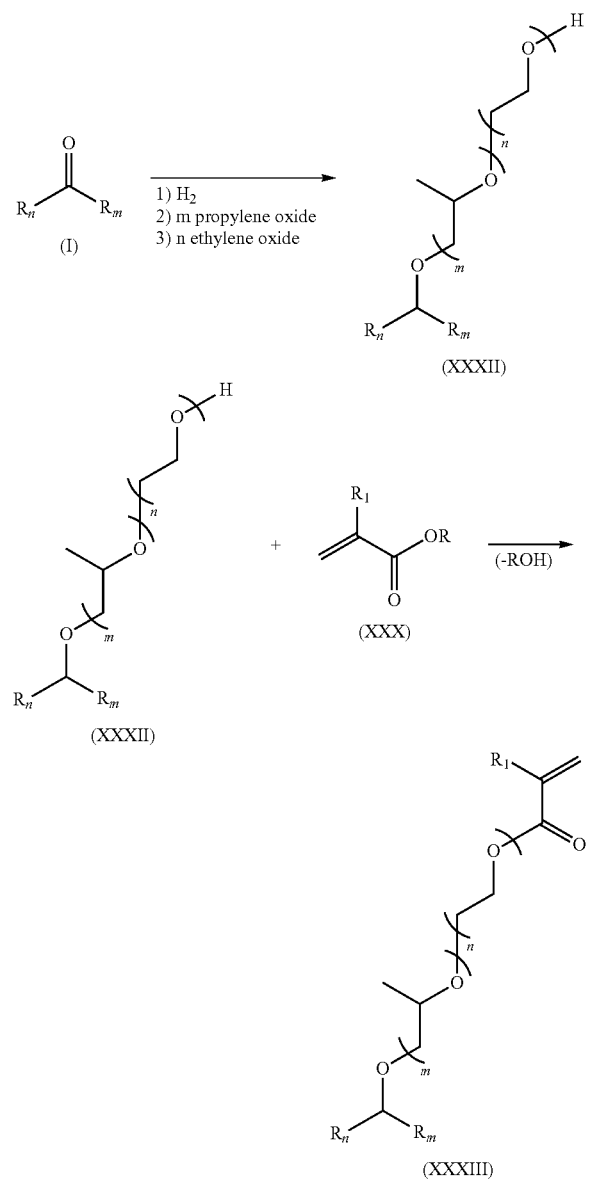

$R_m$ and $R_n$ are as defined in part 1.1, and m and n are integers ranging from 0 to 40 but m and n cannot be both equal to 0.

R and $R_1$ have the same meaning as in part 8.1.

According to the above reaction scheme, at least one ketone (I) is hydrogenated using standard hydrogenation conditions, then condensed with m equivalents of propylene oxide and/or n equivalents or ethylene oxide (e.g. with m equivalents of propylene oxide followed by n equivalents of ethylene oxide).

Standard conditions for secondary alcohols alkoxylations are generally used in order to afford the at least one intermediate (XXXII).

The intermediate (XXXII) is then reacted with at least one acrylate derivative (XXX) according to a transesterification reaction in order to afford at least one other acrylate derivative (XXXIII).

This last reaction is advantageously carried out by contacting both reactants in a reaction zone at a temperature ranging from 15° C. to 400° C.

The reaction can be catalyzed either by acids or by bases. As example of suitable acids, one can mention $H_2SO_4$, HCl, triflic acid, p-toluenesulfonic acid, $AlCl_3$, metal triflate compounds such as aluminium triflate, bismuth triflate, heterogeneous solid acids such as Amberlyst resins, zeolithes etc.

As examples of suitable bases, one can mention NaOH, KOH, MgO, $Na_2CO_3$, NaOMe, NaOEt, tBuOK or $NEt_3$.

The reaction can be carried out in a suitable solvent such as methanol, ethanol, isopropanol, DMSO, THF, methyltetrahydrofuran, toluene, xylenes, water, dioxane or a mixture thereof.

The acrylate derivative (XXX) can be added progressively in the reaction medium in order to avoid side-polymerization to occur.

8.3) Synthesis of a Second Monomer

The at least one end compound can be a compound of formula (XXXIV)

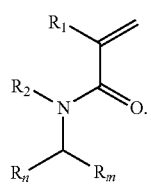

(XXXIV)

Such a compound, which also contains an ethylenic carbon-carbon double bond, is likewise suitable to undergo a radical polymerization.

It can be prepared from a certain twin-tail amine of formula (III), namely an a primary of secondary twin-tail amine of formula (III$^{5'}$)

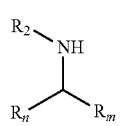

(III$^{5'}$)

wherein:

$R_m$ and $R_n$ are as defined in part 1.1;

$R_2$ is selected from hydrogen or a linear or branched hydrocarbon radical having 1 to 24 carbon atoms which can be optionally substituted and/or interrupted by one or more heteroatoms or hereroatom containing groups; for example, $R_2$ can be selected from H, $-CH_3$, $-CH_2CH_3$, propyl, isopropyl, butyl, sec-butyl, isobutyl and tert-butyl.

At least one amine (III$^{5'}$) prepared according to part 1.1 is reacted with at least one acrylate derivative (XXX) under suitable conditions that prevent conjugate addition to occur in order to afford at least one acrylamide (XXXIV).

The reaction scheme is as follows:

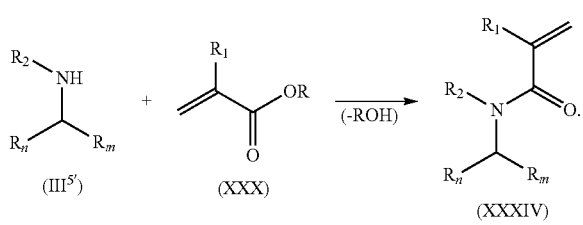

In compounds (XXX) and (XXXIV), R and $R_1$ have the same meaning as in part 8.1.

The reaction is advantageously carried out by contacting both reactants in a reaction zone at a temperature ranging from 15° C. to 400° C.

The reaction can be catalyzed by acids or bases. As example of suitable acids one can mention $H_2SO_4$, HCl, triflic acid, p-toluenesulfonic acid, $AlCl_3$, metal triflate compounds (such as aluminium triflate, bismuth triflate), heterogeneous solid acids such as Amberlyst resins, zeolithes, etc. As examples of suitable bases, one can mention NaOH, KOH, MgO, $Na_2CO_3$, NaOMe, NaOEt, tBuOK, $NEt_3$ etc.

The reaction can be carried out in a suitable solvent such as methanol, ethanol, isopropanol, DMSO, THF, methyltetrahydrofuran, toluene, xylenes, water, dioxane or a mixture thereof.

As an alcohol ROH is generated during the reaction as a side product, it can be removed thanks to distillation in order to drive the reaction toward the desired product (XXXIV).

The acrylate derivative (XXX) can be added progressively in the reaction medium in order to avoid side-polymerization to occur.

8.4) Synthesis of a Branched Fatty Acid

The end compound can be a branched fatty acid of formula (XXXV), as obtainable by the following reaction:

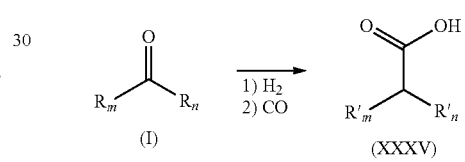

In a first stage, at least one ketone (I) with $R_m$ and $R_n$ being defined as in part 1.1 is hydrogenated to afford the corresponding secondary alcohol. Standard hydrogenation conditions can be used.

This alcohol is then engaged in a carbonylation reaction to afford at least one end product (XXXV).

The carbonylation reaction is advantageously carried out by reacting the secondary alcohol under a CO pressure (typically from 1 atm to 200 bar), in a reaction zone at a temperature usually ranging from 15° C. to 400° C.

The reaction can be optionally carried out in the presence of a suitable solvent and the skilled person of the art will choose the most suitable solvent. Importantly, the reaction can be catalyzed by transition metal based catalysts (for example Co, Rh, Ir and Pd based homogeneous catalyst).

Usually, a halide based promoter is necessary for the reaction to occur. Preferably, the promoter is an iodide, such as HI.

Importantly, during the reaction significant isomerization may occur and mixture of isomeric products (XXXV) may be obtained having their alkyl substituents $R'_m$ and $R'_n$ different from the initial alkyl substituents $R_m$ and $R_n$ present in the starting ketone (I). Thus, in formula (XXXV) specifically, $R'_m$ and $R'_n$ fall under the same general definition of $R_m$ and $R_n$ although being possibly specifically different from initial $R_m$ and $R_n$ of starting ketone (I).

8.5) Synthesis of Polyamines

The end compound can be a polyamine, especially a polyamine of formula (XXXVII):

(XXXVII)

Such a polyamine can be prepared using at least one internal ketone (I') as starting material, with R'$_m$ and R'n being defined as in part 1.2, according to the following reaction scheme:

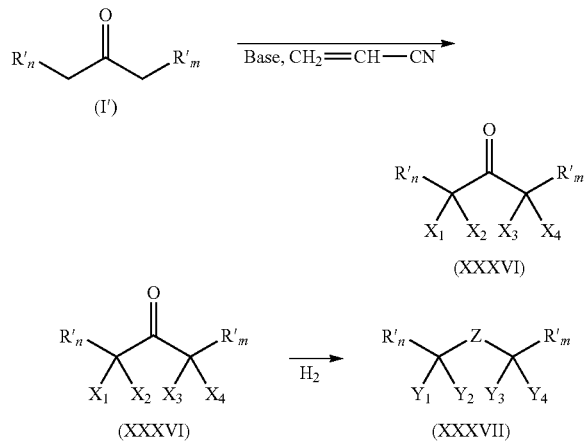

X$_1$, X$_2$, X$_3$ and X$_4$ independently represent a hydrogen atom or —CH$_2$'CH$_2$—CN but all cannot be hydrogen, meaning that at least one of X$_1$, X$_2$, X$_3$ and X$_4$ is —CH$_2$—CH$_2$—CN.

Y$_1$, Y$_2$, Y$_3$ and Y$_4$ independently represent a hydrogen atom or —CH$_2$—CH$_2$—CH$_2$—NH$_2$ but all cannot be hydrogen, meaning that at least one of Y$_1$, Y$_2$, Y$_3$ and Y$_4$ is —CH$_2$—CH$_2$—CH$_2$—NH$_2$.

Z can be either a carbonyl group (C=O) or a carbinol (CH—OH) group or a mixture thereof.

Thus, at least one ketone (I') is first condensed with acrylonitrile to afford at least one intermediate of formula (XXXVI).

The reaction is advantageously carried out by contacting both reactants in a reaction zone at a temperature ranging generally from 15° C. to 400° C. and in the presence of an optional solvent such as methanol, ethanol, isopropanol, DMSO, THF, methyltetrahydrofuran, toluene, a xylene, water, dioxane or a mixture thereof.

The reaction can be catalyzed by a suitable base such as for example NaOH, KOH, MgO, Na$_2$CO$_3$, NaOMe, NaOEt, tBuOK or NEt$_3$.

Optionally and possibly preferably, the reaction is carried out by adding acrylonitrile progressively in the reaction medium in order to avoid side polymerizations, and acrylonitrile can be used in stoichiometric excess. The acrylonitrile in excess can be recovered and recycled.

Mixture of products (XXXVI) with different substituents X$_n$ (n=1 to 4) can be obtained.

In a second step, at least one (poly)nitrile derivative (XXXVI) is hydrogenated to afford the at least one corresponding (poly)amine (XXXVI). Usually, standard conditions for nitrile hydrogenation are used, for example under hydrogen pressure ranging from 1 atm to 200 bar, at a temperature ranging from 15° C. to 400° C., in the presence of an optional solvent and using advantageously a transition metal based catalyst (e.g. Nickel Raney).

A mixture of products (XXXVII) with different Y$_n$ (n=1 to 4) and Z groups can be obtained.

9—Making Secondary Fatty Alcohols, Internal Olefins and Internal Olefin Sulfonates from Internal Ketones 9.1) Use of the Fatty Acid Ketone for the Synthesis of Secondary Fatty Alcohols The fatty acid ketones obtained in accordance with the process P are advantageously used for the manufacture of respective secondary fatty alcohols. To obtain these alcohols the fatty acid ketones obtained in the process P are subjected to a hydrogenation reaction. The reaction is usually carried out using heterogeneous transition metal catalysts on a support in an autoclave with hydrogen gas as hydrogenating agent.

Just by way of example palladium catalysts supported on carbon materials may be mentioned as catalysts. The hydrogenation reaction is usually carried out at a hydrogen pressure of from 500 to 5000 kPa and at a temperature in the range of from 120 to 200° C. without the use of an added solvent.

9.2) Use of the Secondary Fatty Alcohols for the Synthesis of Internal Olefins

The secondary alcohols obtained as described above may be further converted to internal olefins by a dehydration reaction.

Preferably, the dehydration is carried out in the substantial absence of an added solvent, preferably in the absence of added solvent, using aluminum oxide, preferably η-Al$_2$O$_3$ as catalyst at a temperature in the range of from 250 to 350° C. and for a time of 30 min to 6 h.

The internal olefins obtained after the dehydration as described above show a very low degree of isomerization of the double bond. The double bond is formed next to the alcohol group which is removed and so the olefins are internal olefins having the double bond mainly in the middle of the chain. It is apparent that the structure of the olefin obtained is mainly determined by the structure of the starting alcohols. The dehydration reaction is usually carried out in an inert atmosphere.

9.3) Sulfonation of the Internal Olefins

The internal olefins obtained after the dehydration described above can be sulfonated followed by an alkaline hydrolysis to obtain internal olefin sulfonates which are useful as surfactants.

According to a first alternative, the sulfonation can be carried out using a falling film reactor, possibly a lab scale film reactor. This reactor may be equipped with a cooling jacket supplied with cold water in order to prevent temperature increases in the reactor due to the high exothermicity of the reaction. For this reaction, the temperature of the cooling jacket is usually set-up at around 0° to 8 C.

A gas flow consisting of a mixture of sulfonating agent (e.g. anhydrous SO$_3$) diluted with carefully dried inert gas (e.g.nitrogen or air) at a concentration usually in the range of from 0.5 to 10, preferably of from 1 to 5% v/v (particularly preferred around 2.5% v/v) is contacted with a falling film of liquid olefins. The flows of gas and liquid phases are set-up in order to ensure a residence time of from 10 seconds to 10 min, preferably of from 1 min to 6 min (e.g. 3 minutes) in the reactor and a mole ratio SO$_3$:Internal olefin in the range of from 0.7:1 to 1.5:1, preferably of from 0.8:1 to 1.2:1 and most preferably of from 0.9:1 to 1.1:1 (e.g. most preferably of 1.05:1).

When using a mixture of internal olefins with different chain lengths (and thus different molecular weights) the total molar flow of internal olefins can be calculated using the average molecular weight of the mixture of olefins.

Following the sulfonation reaction the mixture exiting the reactor (composed mainly of β-sultones) can be allowed to age in order to allow trans-sulfonation to occur and to increase the conversion of starting olefins.

Thereafter, the obtained mixture can be neutralized using an aqueous solution of a base (e.g.NaOH) in a reactor which is preferably equipped with a mechanical stirring. Hydrolysis is then carried out by heating the mixture under mechanical stirring. During this stage of the process, the β-sulfone is transformed into to desired Internal Olefin Sulfonates through a ring opening reaction.

The sulfonation, digestion and hydrolysis reactions can be followed using NMR analysis. At the end of the process the amount of water in the medium may be adjusted in order to reach an aqueous solution of Internal Olefins Sulfonates with a desired concentration of active matter.

According to a $2^{nd}$ embodiment the sulfonation may be carried out in a (batch) reactor equipped with a mechanical stirring in the liquid phase using an in-situ prepared sulfonating reagent, e.g. "SO₃-dioxane". This embodiment is now described by way of an example.

In a round bottom flask anhydrous dioxane and anhydrous trichloromethane (mixture ratio 1:2 to 1:5 v/v) are mixed and cooled down to a temperature in the range of from −5 to 10° C., preferably to about 0° C. Then liquid SO₃ (2 molar equivalents) is slowly added under stirring during 10 minutes to generate the complex SO₃-dioxane which precipitates out from the mixture as white crystals.

The internal olefins (1 equivalent) are then slowly added under stirring at a temperature of from −5 to 10° C., preferably about 0° C., to the reaction medium during a period of from 0.3 to 3 h, preferably during appr. 1 hour and the mixture is allowed to warm up to room temperature. During this time the color of the mixture changes from light yellow to dark brown and NMR analysis indicates that almost full completion of internal olefins has occurred (around 94% of olefin conversion to sultones). All the volatiles (CHCl₃ and dioxane) are then removed under vaccum.

Then 2.4 equivalents of an aqueous NaOH solution (10 wt %) are added to the residue and the resulting mixture is stirred at room temperature during appr. 1 hour in order to ensure complete neutralization.

Hydrolysis is then performed by stirring the resulting reaction mixture at 95° C. overnight. NMR analysis indicates full conversion of sultones to internal olefin sulfonates.

At the end of the process the amount of water is adjusted in order to reach an aqueous solution of Internal Olefins Sulfonates with a suitable concentration of active matter, e.g. 30 wt %.

10—Particular Embodiments of Method M

In a first particular embodiment of the invented method M, when the internal ketone is caused to react by being subjected to a hydrogenation reaction to obtain a secondary alcohol (as in part 9.1), the so-obtained secondary alcohol may be an intermediate that is in turn caused to react in accordance with a single or multiple reaction scheme that does not include a dehydration reaction that would convert said internal secondary alcohol into an internal olefin (as in part 9.2) as an intermediate or as the end compound.

In another particular embodiment of the invented method M, the end compound differs from an α-sulfocarbonyl compound C1* of of formula (1)

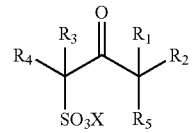

from an α-sulfocarbonyl compound C2* of formula (2)

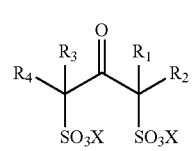

and from a mixture thereof, wherein in above formulae (1) and (2)

$R_1$, $R_3$ and $R_5$, which may be the same or different at each occurrence, are hydrogen or a linear or branched alkyl chain having 1 to 20 carbon atoms, $R_2$ and $R_4$, which may be the same or different at each occurrence, are a linear or branched alkyl group having 4 to 24 carbon atoms and in which the alkyl chain may comprise one or more cycloaliphatic groups, and X is H or a cation forming a salt with the sulfonate group.

Valuable Compounds Preparable by the Method M

It is a last object of the present invention to provide new valuable compounds, with a particular interest for surfactants.

This last object of the present invention is achieved by a variety of compounds, notably surfactants, susceptible of being prepared by the method M as above described.

Many of these compounds can be characterized by their twin-tail or Gemini structure.

Thus, the present invention concerns also:

a compound of formula (III) as previously described, in particular a compound of formula (III'), a compound of formula (III"), a compound of formula (III³'), a compound of formula (III⁴') or a compound of formula (I⁵') as previously described;

a compound of formula (Va) as previously described, a compound of formula (Vb) as previously described or a mixture thereof;

a compound of formula (VII) as previously described;

a compound of formula (VIIIa) as previously described, a compound of formula (VIIIb) as previously described or a mixture thereof;

a compound of formula (X) as previously described;

a compound or a mixture of compounds of general formula (XIa) as previously described;

a compound or a mixture of compounds of general formula (XIb) as previously described;

a compound of a mixture of compounds of general formula (XII) as previously described;

a compound of a mixture of compounds of general formula (XIIIa) as previously described;

a compound of a mixture of compounds of general formula (XIIIb) as previously described;

a compound of formula (XIV) as previously described;

a compound of formula (XVa) as previously described, a compound of formula (XVb) as previously described or a mixture thereof;

a compound of formula (XVIa) as previously described, a compound of formula (XVIb) as previously described or a mixture thereof;

a compound of formula (XVIIa) as previously described;

a compound of formula (XVIIb) as previously described;

a compound of formula (XVIIIa) as previously described, a compound of formula (XVIIIb) as previously described or a mixture thereof;

a compound of formula (XIXa) as previously described, a compound of formula (XIXb) as previously described or a mixture thereof;

a compound of formula (XXI) as previously described;

a compound of formula (XXII) as previously described;

a compound of formula (XXIV) as previously described;

a compound of formula (XXV) as previously described;

a compound of formula (XXVIa) as previously described, a compound of formula (XXVIb) as previously described or a mixture thereof;

a compound of formula (XXVIIa) as previously described, a compound of formula (XXVIIb) as previously described or a mixture thereof;

a compound of formula (XXVIII) as previously described;

a compound of formula (XXIX) as previously described;

a compound of formula (XXXIa) as previously described, a compound of formula (XXXIb) as previously described or a mixture thereof;

a compound of formula (XXXII) as previously described;

a compound of formula (XXXIII) as previously described;

a compound of formula (XXXIV) as previously described;

a compound or a mixture of compounds of general formula (XXXV) as previously described;

a compound or or a mixture of compounds of general formula (XXXVI) as previously described; and a compound or or a mixture of compounds of general formula (XXXVII) as previously described.

SUMMARY OF THE ADVANTAGES OF THE PRESENT INVENTION

The process P of the present invention thus offers an easy access to internal ketones. The process P yields the desired ketones in high yield with only minor amounts (if at all) of undesired by-products being obtained and which can be easily separated from the reaction mixture.

The internal ketones may be separated from the reaction mixture by convenient and economic processes and the catalytic material can be used for several catalytic cycles without significant deterioration of catalytic activity.

As thoroughly shown, the internal ketones are versatile starting materials that can be easily converted into a variety of valuable end compounds through the method M.

The method M of the present invention, since it is based on the process P, thus likewise offers an easier access to these compounds.

Many end compounds obtainable by the method M are useful as surfactants.

Many other compounds obtainable by the method M are useful as intermediates that can in turn be converted into valuable end compounds like surfactants.

EXAMPLES

Example 1

Synthesis of $C_{15}$-$C_{35}$ Ketones Cut Starting from a $C_8$-$C_{18}$ Coco Saturated Fatty Acids Cut Using Magnetite ($Fe_3O_4$) as the Catalyst (12.5 mol % of Fe)

The reaction was carried out under argon in a 750 mL reactor equipped with mechanical stirring, Dean Stark apparatus and an addition funnel. In the reactor, 9.3 g (0.04 mol) of magnetite $Fe_3O_4$ were dispensed and 200 g (0.97 mol) of the coco saturated fatty acids cut (with the following distribution: C8: 7 wt %, C10: 8 wt %, C12: 48 wt %, C14: 17 wt %, C16: 10 wt %, C18: 10 wt %) was introduced into the addition funnel.

A first partial amount of 50 g of fatty acids was added into the reactor and the temperature was brought to $T_1=290°$ C. The mixture was stirred at this temperature during 4 hours. During this time the color of the media changed to black and $H_2O$ was formed. FTIR analysis of the crude mixture showed complete formation of intermediate iron carboxylate complexes.

The temperature was then raised to $T_2=330°$ C. and the mixture was stirred at this temperature during 2 hours. During this time the intermediate iron carboxylate complexes were decomposed to fatty ketones, iron oxide and $CO_2$. The remaining fatty acids (150 g) are slowly introduced into the reactor such that the temperature of the reaction medium didn't fall down below 320° C. and at a flow rate which allowed keeping concentration of fatty acids in the reaction medium very low (for example with an addition flow rate of around 25 g fatty acids/hour).

Practically this was done through the successive slow additions (1 hour per addition) of 3 portions of 50 g of melted fatty acids with 1 hour of stirring at 330° C. between each addition.

At the end of the last addition, the crude medium is stirred at 330° C. during 2 hours and the reaction progress is monitored through FTIR. When the reaction is completed (no more iron complex detected by FTIR), the mixture is allowed to cool down at room temperature and 400 mL of $CHCl_3$ is added to the crude media. The mixture is stirred at 40° C. in order to solubilize the product. The obtained suspension was filtered on a silica plug (400 g) and eluted using 3 L of chloroform. Evaporation of the solvent afforded 160 g (0.456 mol) of the product $C_{15}$-$C_{35}$ ketones as a white wax (94% isolated yield) analytically pure.

Example 2

Synthesis of $C_{15}$-$C_{35}$ Ketones Cut Starting form a $C_8$-$C_{18}$ Coco Saturated Fatty Acids Cut Using Magnetite ($Fe_3O_4$) as the Catalyst (Molar Ratio Iron Metal:Carboxylic Acid Equivalent 1.2:22.1 or 5.4 mol %)

The reaction was carried out under an inert atmosphere in a 7.5 L INOX 316 L jacketed reactor equipped with a mechanical strirrer and an exhaust tube in order to remove gas ($H_2O$ and $CO_2$) generated during the reaction. The reactor was connected thanks to a insulated tube to a heated glass vessel containing 4093 g (19.7 moles) of the coco saturated fatty acids cut $C_8$-$C_{18}$ (with the following composition: C8: 7.7 wt %, C10: 6.2 wt %, C12: 48.4 wt %, C14: 18.2 wt %, C16: 9.1 wt %, C18: 9.9 wt %).

93 g of magnetite $Fe_3O_4$ (0.4 mol) followed by 503 g (2.4 mol) of the cut of saturated fatty acids $C_8$-$C_{18}$ were directly added into the reactor. The temperature of the media inside the reactor was progressively increased to $T_1=290°$ C. and the mixture was allowed to stir (140 rpm) during 4 h00 until complete disappearance of fatty acids and formation of intermediate iron carboxylate complex were observed by FTIR. Generation of water is observed during this step. Then the temperature inside the reactor was progressively increased to $T_2=310°$ C. and stirred at this temperature during 2 h00 in order to decompose the intermediate iron carboxylate complex to ketone, $CO_2$ and iron oxide. The remaining melted fatty acids (4093 g) contained in the bottle were then slowly added into the reactor (thanks to a slight overpressure maintained in the bottle) at a flow which allows keeping the reaction media temperature slightly above 310° C. (310° C.-315° C.) and which avoids the accumulation of fatty acids inside the reactor (this can be checked easily thanks to regular FTIR analysis). Practically this has been achieved with a total addition duration of 14 h30.

At the end of the addition, the reaction mixture was allowed to stir at 310° C. during an additional 5 h00 until complete disappearance of intermediate iron carboxylate complex was observed by FTIR.

When the reaction was completed, the mixture was allowed to cool down at 80° C. and the crude was removed from the reactor, cooled down at room temperature and crushed into powder.

The obtained product was dissolved into 25 L of $CH_2Cl_2$ and the resulting suspension filtered in order to remove insoluble iron oxide.

The filtrate was washed several times using an aqueous solution of $H_2SO_4$ in order to remove soluble iron species from the product. The organic phase was dried, filtered and the solvent was evaporated under vaccuum to furnish 3750 g (10.6 moles) of the product fatty ketones as a dark brown wax (95% isolated yield) analytically pure.

Should the disclosure of any patents, patent applications, and publications which are incorporated herein by reference conflict with the description of the present application to the extent that it may render a term unclear, the present description shall take precedence.

The invention claimed is:

1. A process P for the decarboxylative ketonization of fatty acids, fatty acid derivatives or mixtures thereof in liquid phase with metal compounds as catalysts, the process comprising:
    a) in a first step, elementary metal or a metal compound, said elementary metal or metal compound being selected from the group consisting of iron, iron (II) oxide, a mixed oxide of iron (II) and iron (III), magnesium and magnesium oxide, and at least one fatty acid, at least one fatty acid derivative or a mixture thereof comprising at least 10 mol %, based on the entire amount of fatty acid or fatty acid derivative, of fatty acid having 12 carbon atoms or less or derivative of fatty acid having 12 carbon atoms or less, are mixed in a molar ratio of from 1:0.8 to 1:3.5, wherein the molar ratio is of the elementary metal or metal compound to the total amount of carboxylic groups in the at least one fatty acid, at least one fatty acid derivative or a mixture thereof, and reacted for a period $P_1$ of from 5 min to 24 h at a temperature $T_1$ which is above 270° C. and below 300° C. in the absence of added solvent, and
    b) thereafter the temperature is raised to a temperature $T_2$ which ranges from 300° C. to 400° C., and additional fatty acid, fatty acid derivative or a mixture thereof comprising at least 10 mol %, based on the entire amount of fatty acid or fatty acid derivative, of fatty acid having 12 carbon atoms or less or derivative of such fatty acid, is added over a period of time $P_2$ of from 5 min to 24 h in the absence of added solvent until the molar ratio of the elementary metal or metal compound to the total amount of carboxylic groups in the at least one fatty acid, at least one fatty acid derivative or a mixture thereof is in the range of from 1:6 to 1:99.

2. The process in accordance with claim 1 wherein temperature $T_1$ is from 272° C. to 298° C.

3. The process in accordance with claim 1 wherein
    temperature $T_1$ is from 275° C. to 295° C.
    period of time $P_1$ is from 5 min to 360 min, and
    period of time $P_2$ is from 15 min to 18 h.

4. The process in accordance with claim 1 wherein temperature $T_2$ is in the range of from 305° C. and up to 380° C.

5. The process in accordance with claim 1 wherein the difference of temperature $T_2$-$T_1$ ranges from 15° C. to 50° C.

6. The process in accordance with claim 1 wherein water formed during the reaction is continuously removed from the reaction mixture.

7. The process in accordance with claim 1 wherein step a) is carried out at a temperature $T_1$ of from 280° C. to 295° C. for a duration of from 15 min to 360 min and the fatty acid, fatty acid derivative or mixture thereof in step b) is added over a period $P_2$ of from 2 hours to 16 hours.

8. The process in accordance with claim 1 wherein, after the temperature has been raised to $T_2$ and before the additional fatty acid, fatty acid derivative or mixture thereof is added over period of time $P_2$, said temperature is maintained at temperature $T_2$ during a period of time $P_{12}$ of from 30 min to 300 min.

9. The process in accordance with claim 1 wherein, after the additional fatty acid, fatty acid derivative or mixture thereof has been added over period of time $P_2$, the temperature is maintained at temperature $T_2$ during a period of time $P_{23}$ of from 30 min to 300 min.

10. The process in accordance with claim 1 wherein at the end of step b) the metallic compounds are separated from the products using distillation at reduced pressure, application of a magnetic field, or simple filtration and then are recycled for the conversion of another batch of fatty acid or fatty acid derivative or a mixture thereof comprising at least 10 mol %, based on the entire amount of fatty acid or fatty acid derivative, of fatty acid having 12 carbon atoms or less or derivative of such fatty acid.

11. The process according to claim 1, wherein an internal ketone manufactured through the decarboxylative ketonization of the fatty acid, fatty acid derivative or mixture thereof is subjected to a hydrogenation reaction to manufacture a secondary fatty alcohol.

12. The process according to claim 11, wherein the secondary fatty alcohol is further converted to an internal olefin by a dehydration reaction.

13. The process according to claim 12, wherein the internal olefin obtained after the dehydration is sulfonated followed by an alkaline hydrolysis to obtain an internal olefin sulfonate.

14. The process in accordance with claim 2 wherein temperature $T_1$ is from 275° C. to 295° C.

15. The process in accordance with claim 3 wherein temperature $T_1$ is from 280° C. to 295° C.

16. The process in accordance with claim 1, wherein the elementary metal or metal compound is selected from the group consisting of iron powder, magnetite and magnesium oxide.

17. The process in accordance with claim 1, wherein the elementary metal or metal compound is iron powder.

18. The process in accordance with claim 1, wherein the elementary metal or metal compound is magnetite.

19. The process in accordance with claim 1, wherein the elementary metal or metal compound is magnesium oxide.

* * * * *